US012682982B2

(12) United States Patent
Chen et al.

(10) Patent No.: US 12,682,982 B2
(45) Date of Patent: Jul. 14, 2026

(54) SYSTEMS AND METHODS FOR CORRECTING FOR NOISE AND SYSTEMIC VARIATIONS IN SEQUENCING DATA

(71) Applicant: Regeneron Pharmaceuticals, Inc., Tarrytown, NY (US)

(72) Inventors: Lei Chen, Tarrytown, NY (US); Charles Paulding, Tarrytown, NY (US); Amy Damask, Tarrytown, NY (US); Hyun Min Kang, Tarrytown, NY (US); Alicia Hawes, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 18/422,789

(22) Filed: Jan. 25, 2024

(65) Prior Publication Data

US 2024/0404627 A1      Dec. 5, 2024

Related U.S. Application Data

(60) Provisional application No. 63/441,308, filed on Jan. 26, 2023.

(51) Int. Cl.
*G16B 20/20* (2019.01)
*G16B 30/10* (2019.01)

(52) U.S. Cl.
CPC ............. *G16B 20/20* (2019.02); *G16B 30/10* (2019.02)

(58) Field of Classification Search
CPC ................................. G16B 20/20; G16B 30/10
See application file for complete search history.

(56) References Cited

U.S. PATENT DOCUMENTS

2014/0051588 A9   2/2014   Drmanac et al.
2015/0051087 A1   2/2015   Rabinowitz et al.
(Continued)

OTHER PUBLICATIONS

Amarasinghe, S.L., Su, S., Dong, X. et al. Opportunities and challenges in long-read sequencing data analysis. Genome Biol 21, 30 (2020). https://doi.org/10.1186/s13059-020-1935-5 (Year: 2020).*
(Continued)

*Primary Examiner* — Larry D Riggs, II
*Assistant Examiner* — Emilie A Smith
(74) *Attorney, Agent, or Firm* — Armstrong Teasdale LLP

(57) ABSTRACT

The disclosure generally pertains to providing an accurate genotype for high repeat genes. First, repeat structures of sequencing reads are identified and sequence reads with abnormal repeat structures are removed to generate a first dataset. The sequence reads of the first dataset are filtered to exclude sequences with structural artifacts to generate a second dataset. Data from the second dataset is input to a model to generate a third dataset, the third dataset including sequencing reads categorized by allele. Next, a consensus sequence is generated for each allele in the third dataset to generate a fourth dataset of consensus reads for all alleles in the third dataset. Each allele of the fourth dataset is translated to generate a fifth dataset, the fifth dataset including the corresponding amino-acid sequence of each allele. A protein-altering variant status is then determined based on the amino-acid sequences of the fifth dataset.

20 Claims, 29 Drawing Sheets

(56) References Cited

U.S. PATENT DOCUMENTS

| 2021/0257052 A1 | 8/2021 | Van Rooyen et al. | |
| 2023/0162815 A1* | 5/2023 | Selkov .................. | G16B 30/00 |
| | | | 702/20 |

OTHER PUBLICATIONS

H.S. Girgis, C.D. DuPai, J. Lund, J. Reeder, J. Guillory, S. Durinck, Y. Liang, J. Kaminker, P.A. Smith, E. Skippington, Single-molecule nanopore sequencing reveals extreme target copy number hetero-geneity in arylomycin-resistant mutants, Proc. Natl. Acad. Sci. U.S.A.118 (1) e2021958118, 2021. (Year: 2021).*

* cited by examiner

100

110

GENOTYPING
COMPUTING DEVICE

APP

112

DATABASE

120

USER
COMPUTING
DEVICE

APP (UI)

130

132

THIRD PARTY
DEVICE

140

GENOTYPING
SERVER

150

210

302

308

304

306

PacBio sequencing data for person X:

~60%
13 kb
reads

510

~30%
15 kb
reads

520

Sequencing error    True variant

<10%
reads with abnormal lengths

| Var | Freq. ratio REGN total/gnomad* | Freq. ratio REGN AD/gnomad | Freq gnomad (N=141k) | Freq. REGN total (N=3060) | Freq. REGN AD (N=1560) | Freq. REGN Asthma (N=1500) |
|---|---|---|---|---|---|---|
| p.Arg501Ter (stop gain) | 3.30 | 5.52 | 0.0094 | 0.031 | 0.052 | 0.0093 |
| p.Ser761Cysfs (frameshift) | 3.15 | 5.03 | 0.013 | 0.041 | 0.065 | 0.016 |
| p.Arg2447Ter (stop gain) | 2.65 | 4.21 | 0.0029 | 0.0077 | 0.012 | 0.003 |
| pLoF burden | 2.61 | 4.13 | 0.046** | 0.12 | 0.19 | 0.044 |

1702
1704
1706
1708

FIG. 17 beta = -0.44, p = 3.72e-05
p_RINT = 4.57e-05 complete FLG repeats before pLoF (sum of two alleles)
1908 beta = -0.19, p = 0.0005
p_RINT = 8.7e-04 complete FLG repeats before pLoF (sum of two alleles)
1908

History of asthma

History of Food allergy

History of atopic dermatitis

History of Food allergy

SYSTEMS AND METHODS FOR CORRECTING FOR NOISE AND SYSTEMIC VARIATIONS IN SEQUENCING DATA

CROSS-REFERENCE TO RELATED APPLICATIONS

This application claims priority to U.S. Provisional Patent Application No. 63/441,308, filed on Jan. 26, 2023, which is incorporated by reference herein in its entirety.

FIELD

This disclosure relates generally to correcting for noise and system variations in sequencing data and more particularly, to systems and methods to correct for noise and systemic variations in sequencing data created by repeat regions.

BACKGROUND

Genotyping allows researchers to determine the DNA sequence of an individual at a specific locus in their DNA. Due to the advancement of genetic sequencing technologies, researchers are now able to investigate individual genes for common variants, thereby allowing for the investigation of disease-causing variants across a population.

Currently, genotyping is accomplished by conventional genotyping methods using pre-defined single nucleotide polymorphisms, or by direct sequencing.

Conventional genotyping usually requires pre-defined single nucleotide polymorphisms ("SNP") markers that must be discovered and validated in advance. These markers are often population-specific, and thus must be detected in each population sample before genotype can be assessed. SNPs are typically detected via hybridization or by individual SNP-specific PCR-based assays. Thus, it can be inefficient to establish the required SNP markers across the database due to the intensive labor required to define the SNPs prior to genotyping.

Genotyping by Sequencing (GBS) technology enables the detection of a wider range of polymorphisms than PCR-based assays such as insertions or deletions ("indels"), in addition to SNPs. The main advantage of sequencing vs. genotyping arrays is arrays are fixed for content but sequencing allows you to discover novel variants. GBS allows for a more accurate assessment of individuals in a population, as researchers can detect a wider variety of mutations among individuals in a dataset. GBS technology eliminates the need to pre-discover and validate polymorphisms as required in conventional genotyping. Thus, GBS greatly reduces the labor requirement for genotyping, and can be used in any polymorphic species and any segregating population.

However, there are several drawbacks to GBS. First, GBS requires double-stranded adaptors for site specific ligation to primers for amplification. The methods required to ligate the adapters to the sequences of interest prior to sequencing require stringent control of the template to adaptor concentration ratio in the adaptor ligation. As a result, precisely quantified, high quality input DNA is required as a starting material (see, e.g., Elshire et al.). Second, these methods survey hundreds of thousands or more sites and thus require numerous sequencing reads to generate enough coverage for each site in each sample. Thus, while GBS is less labor intensive than conventional sequencing, the method still requires a significant amount of labor to accomplish.

The proliferation of Next-Generation Sequencing technology ("NGS") has provided a tremendous opportunity to genotype individuals in depth and to discover novel genetic variation.

However, certain genes have still proved to be difficult to genotype, in spite of the advances in NGS. Specifically, genes that include large repeat structures in their nucleic acid code have proven difficult to genotype, due to inherent limitations of the NGS technology.

Genotyping requires sequencing data produced by a sequencing platform as input data. The quality of sequencing data varies widely among platforms and technologies, and directly impacts the quality of the genotyping. Therefore, a basic understanding of sequencing is required.

Currently, the standard platforms for sequencing utilize Next-Generation Sequencing technology ("NGS"), such as that produced by Illumina® sequencing-by-synthesis technology. NGS technologies produce "short-read" data, or sequencing data that is in small fragments of DNA, typically around 150 nucleotides in length. To accomplish sequencing, NGS technologies reduce the DNA sequence of sample into many small fragments, in a step called "library preparation." Once the library has been prepared, the DNA fragments are replicated into millions of copies, in a process called "amplification." Finally, the amplified fragments are recorded by the sequencer via a biochemical process, to create a digital record of each nucleotide in each fragment. The digital record of each fragment is called a "sequencing read" or "read."

Once sequencing reads have been created, a software is required to "assemble" the DNA sequence of the sample, by mapping sequencing reads to each other to recreate the larger sequence. Assembling large repeat structures is made difficult by the short-read length of NGS data. NGS sequencing reads have an average read length of 150 nucleotides. Thus, the assembly of genes using NGS data requires a broad read depth to create sufficient overlap to determine the correct location of each read in the genome. However, in genes with large repeat regions, broad read depth may not be sufficient to overcome the limitations of short read sequencing, or may further worsen the process, because the short reads covering the repeat regions will map to multiple positions in the repeat sequence. Thus, it is difficult to determine the correct position of the read in the sequence, and often leads to a faulty assembly that is not representative of the sequenced sample.

Long-read data such as that produced by the Pacific Biosciences sequencing method (Pacific Biosciences, Menlo Park, Calif.) ("PacBio") provide a solution for the assembly issues that plague NGS data. Because the reads of long-read data methods such as PacBio exceed the average length of the repeat sequences, assemblies can be appropriately anchored to the correct location of the sample. See, for example, U.S. Pat. No. 9,165,109, the entirety of which is incorporated by reference.

Although certain aspects of the methods herein focus on an alignment of reads produced by PacBio sequencing instruments, such as the PacBio® RS instrument, the characteristics of sequence reads produced by the PacBio® RS instrument are likely to be common to other single molecule sequencing methods. The main differences in read characteristics for single molecule sequencing reads are that they are one to two orders of magnitude longer than reads produced from NGS, and that the sequencing errors are biased towards insertions and deletions at a higher overall error rate than that in NGS sequencing. In contrast to NGS methods, the signals observed in single molecule sequencing do not have the problems of phasing or prephasing (see Kao, et al. (2009) Genome Research 10:1884-1895) where signal is observed from different positions in an amplified template at the same cycle. Fluorescence signal does not decrease across the length of a read, allowing both longer reads and no positional bias in base calling error. The length of reads in the PacBio RS platform is limited by processivity of the polymerase and may be approximated by an exponential process. Base calls are derived from real-time measurements of analog fluorescence during incorporation. A small fraction of the time, bases will incorporate faster than the limit of detection, resulting in deletions in the called sequence. Other times, bases reside in the observation volume but are not incorporated into the growing strand, and give signal that result in insertions in the read. Incorrect bases are rarely incorporated, leaving a very low substitution rate. The effect of this is a bias in the type of error in single molecule sequencing to insertions and deletions. The raw accuracy is lower than NGS sequencing, however due to lack of positional bias in sequencing error the consensus accuracy grows quickly with coverage (see Travers, et al. (2010) Nuc. Ac. Res. 38 (15):e159).

In the context of genotyping, long-read data sequencing assemblies have shown several issues in the quality of data caused by inflated sequencing error rate, junk reads, and other technical artifacts.

SUMMARY

Accordingly, the disclosed methods and systems are directed to providing an accurate genotype for high repeat genes using long-read sequencing data.

Aspects of the present invention describe systems and methods for generating genotype calls for one or more samples using long-read sequencing data. The genotyping approach transforms and corrects for systematic noise in sequencing data created by repeat regions in repeat rich genes.

In one embodiment, the present disclosure provides a method for genotyping high repeat genes of individuals across a dataset, using long-read sequencing data.

In some embodiments, the parameters in the method are associated with noise and other sources of systematic variation. The parameters may then be used to transform a dataset of long read sequencing data into a dataset representation of normalized alleles that accurately represent the genotypes of the samples in the dataset. In various implementations, systematic variation may arise from instrument artifacts, chemistry artifacts, process artifacts, operational artifacts, sequencing artifacts, and assay artifacts. Compensating for noise and systemic variation makes it possible to determine the genotype for the sample. These and other features of the present teachings are set forth herein.

In some embodiments, the present disclosure genotypes individuals by classifying reads by length and removing noise based on expected length of the alleles; determining repeat structure of the remaining reads and removing noise based on the structure of known variants; classifying the remaining reads by allele; identifying protein truncating variants; and identifying novel alleles with previously unknown copy number.

In some embodiments, the denoising of the input data may be accomplished by classifying the reads by length and removing lengths that are inconsistent with known alleles, creating a first dataset of reads by removing said reads from the dataset.

In some embodiments, denoising of the first dataset to create the second dataset may be accomplished by mapping references of the repeat sequences to each of the long-read sequencing reads, and creating readouts of the structure. One non-limiting example is Minimap2:pairwise alignment for nucleotide sequences Li H. Bioinformatics, Volume 34, Issue 18, 15 Sep. 2018, Pages 3094-3100.

In some embodiments, denoising of the first sequencing data to create a second dataset may include the culling of reads from the dataset that are found to have inappropriate structure as artifacts.

In some embodiments, reads of the second dataset may be transformed into a third dataset, by classifying reads by allele.

In some embodiments, creating a third dataset may include correcting for PCR imbalance, and only including reads that are representative of the alleles of the individual.

In some embodiments, reads of the second dataset may be transformed into a third dataset, that includes a categorization of each samples based on its copy number homogeny.

In some embodiments, transformation of the second to third dataset includes categorizing the individual sample as either a copy number heterogeneous ("CN-HET") or copy number homogeneous ("CN-HOM") individual, based on size ratio of the first and second most common read groups. If the size ratio between the most common read groups is greater than expected, the reads are categorized as CN-HOM. If the size ratio is approximately as expected, they are marked as CN-HET. If the first common read group is longer than that of the second, the sample is categorized based on whether the length of the first group is greater or less than the length of the third group.

In some embodiments, the third dataset is further transformed to a fourth dataset by generating a consensus sequence for each of the alleles of the third dataset.

In some embodiments, transformation of the third dataset to a fourth dataset may include generating a consensus sequence across each allele of the third dataset. The generation of the consensus sequence may be accomplished through the use of a software such as SPOA, as described in Vaser R, Sović I, Nagarajan N, Šikić M. Fast and accurate de novo genome assembly from long uncorrected reads. Genome Res. 2017 May; 27(5):737-746. Epub 2017 Jan. 18.

In some embodiments, the consensus sequence of the fourth dataset may be aligned to a customized reference to identify all nucleic acid changes.

In some embodiments, the consensus sequence of the fourth dataset may be further transformed into a fifth dataset by translating the consensus sequence into the corresponding amino acid code.

In some embodiments, the fourth dataset is transformed into the corresponding amino acid code via the longest open reading frame ("ORF"), using a software program such as the getorf utility in the EMBOSS package, as described in EMBOSS: The European Molecular Biology Open Software Suite (2000), Rice, P. Longden, I. and Bleasby, A. Trends in Genetics 16, (6) pp 276-277.

Specific embodiments may be utilized to genotype the Filaggrin gene. Filaggrin is the most commonly mutated gene associated with atopic dermatitis (AD).

Filaggrin is a repeat rich gene, with 10 to 12 complete repeats in the third exon of the gene. The length of each repeat is between 972 and 975 nucleotides. The complex structure of filaggrin makes sequencing by conventional short read technology highly unreliable and inaccurate. Long-read sequencing is also unreliable when using conventional calling algorithms. The current approach described here, provides a novel approach for determining accurate genotyping for long-read sequencing data for genes (e.g. filaggrin) with complex structures.

BRIEF DESCRIPTION OF THE DRAWINGS

FIG. 17 is a table showing protein truncating variants (PTVs or pLoFs) and the dosage of any PTVs (pLoF burden) observed within the current study, in accordance with an embodiment of the present disclosure.

DETAILED DESCRIPTION

Figure 1:
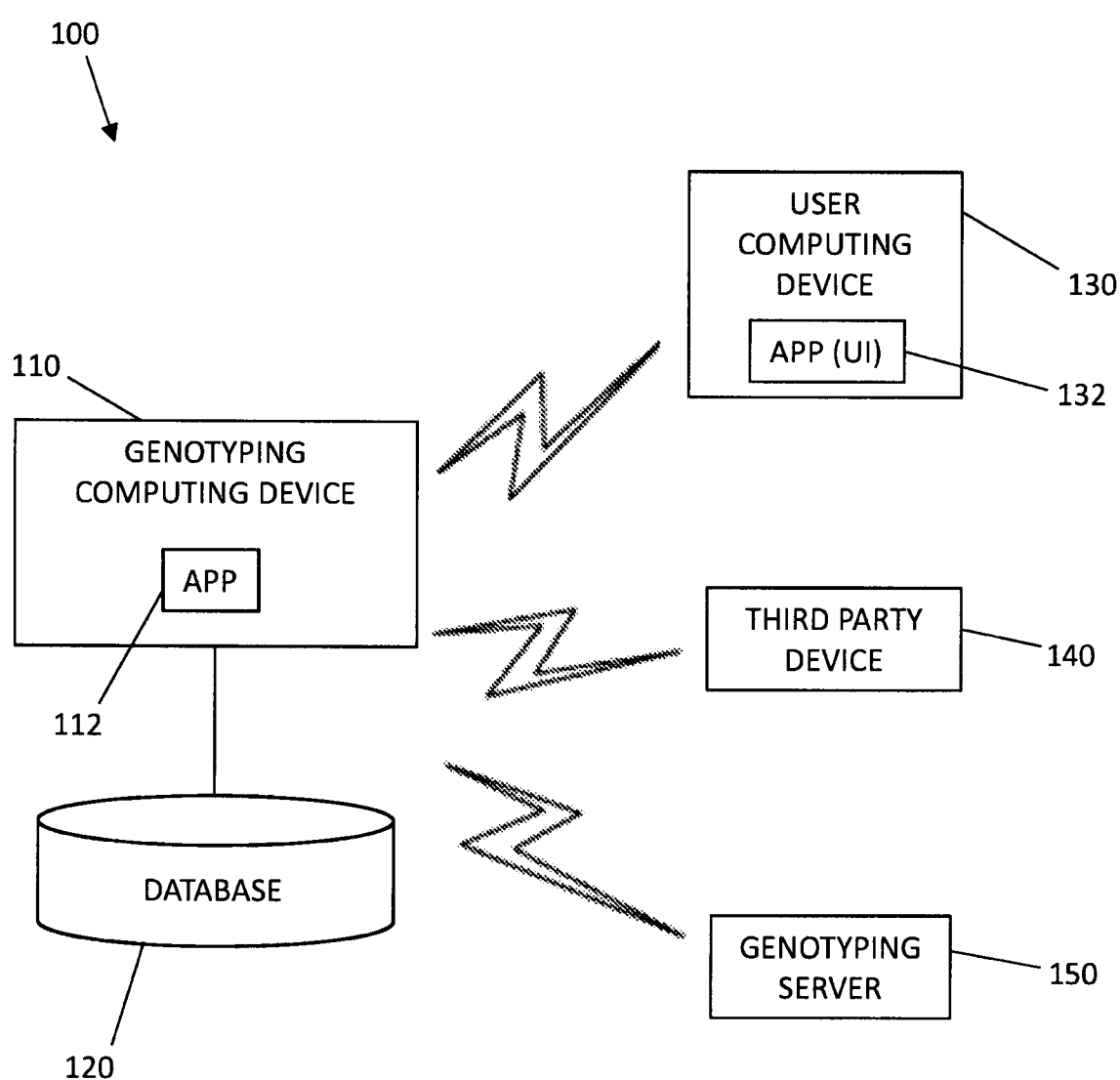
FIG. 1 illustrates a block diagram of an example computer system in accordance with an embodiment of the present disclosure.

Unless described otherwise, all technical and scientific terms used herein have the same meaning as commonly understood by one of ordinary skill in the art to which this invention belongs. Although any methods and materials similar or equivalent to those described herein can be used in the practice or testing, particular methods and materials are now described.

NGS has allowed for significant advances in genotyping technology, and an increased understanding in disease causing variants in the human genome.

However, certain genes have still proved to be difficult to genotype, in spite of the advances in NGS. Specifically, genes that include large repeat structures in DNA sequence have proven difficult to genotype, due to inherent limitations of the NGS technology.

NGS technologies are short read platforms. The sequencing data produced by NGS platforms have an average read length of 150 nucleotides. Due to the short-read nature of NGS data, genome or gene assemblies using NGS data require a broad coverage of the genome or gene of interest to create sufficient overlap to determine the correct location of each read in the genome.

However, in genes with large repeat regions, this process is complicated by the fact that reads covering the repeat regions will map to multiple regions in the gene's sequence. Thus, it can be difficult to determine the correct position of the read in the sequence, and often leads to a faulty assembly that is not representative of the sequenced sample.

Long-read data such as that produced by the PacBio sequencing method provide a solution for the assembly issues that plague NGS data. Because the reads of long-read data methods such as PacBio exceed the average length of the repeat sequences, assemblies can be appropriately anchored to the correct location of the genome.

However, long-read sequencing read assemblies have shown several issues in the quality of data caused by inflated sequencing error rate, junk reads, and other technical artifacts.

The methods of the present disclosure can account for the errors in long-read sequencing reads, allowing for an accurate assembly of the genome.

In one aspect, the present disclosure is directed to providing a method for genotyping individuals using long-read sequencing data, such as that provided by PacBio.

In another aspect, the present disclosure provides a method for denoising the sequencing data provided as an input, allowing for an accurate assembly of the individual sample's DNA sequence.

In another aspect, the present disclosure provides a method for determining an individual's amino acid sequence based on an assembly of their DNA sequence.

In another aspect, the present disclosure provides a method for identifying protein-truncating variants, based on the analysis of the amino acid sequences of individuals across a population, in comparison to a reference amino acid sequence. Individuals in the population with genes that contain an amino acid sequence shorter in length than that of the reference are determined to have protein-truncating variants of the gene.

The term "a" should be understood to mean "at least one" and the terms "about" and "approximately" should be understood to permit standard variation as would be understood by those of ordinary skill in the art, and where ranges are provided, endpoints are included. As used herein, the terms "include," "includes," and "including" are meant to be non-limiting and are understood to mean "comprise," "comprises," and "comprising" respectively.

The term "sequencing read" or "read" should be understood to mean the DNA sequence of a fragment of DNA produced from a sequencer.

The term "read length" should be understood to mean the length of a sequencing read in units of nucleotides.

The term "noise" should be understood to mean statistical anomalies in a dataset that are un-representative of the sample. In the context of DNA sequencing and genotyping, noise can include sequencing artifacts such as insertions or deletions, or errors in the balance of reads for each allele caused by the amplification reaction.

The term "amplified" should be understood to mean DNA sequences that have been replicated for sequencing using an artificial method. Samples are amplified prior to DNA sequencing to increase the number of target sequences to be sequenced, and thus increase the number of reads present in the sequencing data produced by the sequencer.

The term "repeat region" should be understood to mean a region of a DNA sequence that contains a pattern of nucleotides that occur in several copies in said region. Repeated sequences can consist of two to several thousand nucleotides repeated in tandem, and are estimated to constitute approximately 30 percent of the human genome.

The term "DNA segment" should be understood to mean a length of genomic DNA that may be delineated by its ability to be sequenced using DNA probes.

The term "genome" should be understood to mean the DNA or RNA genetic material present within a cell, including the chromosomal/nuclear genome of a cell, as well as any mitochondrial and/or plasmid genome. The nuclear genome can include protein-coding genes, non-coding genes, other functional regions, including non-coding DNA or RNA, and junk DNA or RNA, if present.

The term "protein-coding gene" should be understood to mean sequences of nucleic acid molecules (RNA or DNA molecules) that comprise a nucleotide sequence which encodes a protein. The coding sequence can further include initiation and termination signals operably linked to regulatory elements including a promoter and polyadenylation signal capable of directing expression in the cells of an individual or mammal to which the nucleic acid is administered.

The term "protein-altering variant" should be understood to mean a variant which has an effect on protein structure. The term "protein truncating variants" should be understood to mean genetic variants that are predicted to cause a truncated amino acid chain, after translation. Amino acids can be truncated through the addition of a stop codon, or via a frameshift or missense mutation.

The term "PacBio" should be understood to mean PacBio sequencing, a trademarked sequencing method from Pacific Biosciences.

The term "long read" should be understood to mean sequencing reads in excess of 500 nucleotides in length. Long read data is typically produced via third generation, or Next-Next-Gen, Sequencing platform, and produces an average read length in excess of 10,000 nucleotides (or 10 kb). In contrast, NGS sequencing produces an average read length of 150 nucleotides.

The term "genotyping" should be understood to mean determining the DNA sequence of an individual at a specific locus.

The term "phasing" should be understood as inferring haplotypes from genotype data.

The term "artifact" should be understood to mean an error in the representation of the data caused by the involved equipment.

The term "sequence artifact" should be understood to mean a variation introduced by non-biological processes.

The term "structural artifact" should be understood to mean a sequence with unknown copy numbers compared with exon or subunit structures in a reference gene. The unknown copy numbers may comprise unknown exon or subunit structures (e.g., where there is more than one exon corresponding to each domain). The reference gene may comprise exon structures from one or more known alleles of the gene.

The term "detecting read structure by alignment" should be understood to mean mapping the exon structure of the read to a reference exon structure of a reference gene (e.g., mapping exons which represent repeats).

The term "variant allele frequency" should be understood to mean the frequency of sequence reads observed matching a specific DNA variant.

The term "barcoded amplicon" should be understood to mean a unique identifier ligated to individual samples to index them in sample preparation, prior to sequencing, to maintain sample identity.

The term "CN-HOM" should be understood to mean an individual whose sequencing data for the gene to be genotyped contains a pair of alleles equal in length containing the same number of repeats or same repeat structure.

The term "CN-HET" should be understood to mean an individual whose sequencing data for the gene to be genotyped contains a pair of alleles differing in length, each containing a different number of repeats or same number of repeats, while having different repeat structures.

The term "historical data" should be understood to mean training data. comprising dataset X and allele classification of the sample in the dataset. For example, in some embodiments, a machine learning model is trained to relate a dataset to the allele classification. More particularly, the model finds the relationship between the input (the dataset) and the output (allele classification). Allele classification may comprise, for example, assigning different alleles by heterozygous SNP and/or indel if CN-HOM or by CN structure if CN-HET.

Sequence identity can be calculated using an algorithm, for example, the Needleman Wunsch algorithm (Needleman and Wunsch 1970, J. Mol. Biol. 48:443-453) for global alignment, or the Smith Waterman algorithm (Smith and Waterman 1981, J. Mol. Biol. 147:195-197) for local alignment. Another preferred algorithm is described by Dufresne et al. in Nature Biotechnology in 2002 (vol. 20, pp. 1269-71) and is used in the software GenePAST (GQ Life Sciences, Inc. Boston, Mass.).

Assembly of the reads can be calculated using a software such as SPOA, as described in Vaser R, Sović I, Nagarajan N, Šikić M. Fast and accurate de novo genome assembly from long uncorrected reads. Genome Res. 2017 May; 27(5):737-746 Epub 2017 Jan. 18.

Analysis of sequencing data, alignment, and genomic features can be calculated using a software such as BED-Tools, as described in Aaron R. Quinlan, Ira M. Hall, BEDTools: a flexible suite of utilities for comparing genomic features, Bioinformatics, Volume 26, Issue 6, 15 Mar. 2010, Pages 841-842.

Accordingly, the disclosed methods and systems are directed to providing an accurate genotype for high repeat genes using long-read sequencing data.

Systems and methods for generating genotype calls for one or more samples using long-read sequencing data are disclosed. The genotyping approach transforms and corrects for noise and/or systemic variations in sequencing data created by repeat regions in repeat rich genes.

In one embodiment, the present disclosure provides a method for genotyping high repeat genes of individuals across a dataset, using long-read sequencing data.

In some embodiments, the parameters in the method are associated with the removal of noise and systematic variation.

In some embodiments, the present disclosure genotypes individuals by classifying reads by length and removing noise based on expected length of the alleles; determining repeat structure of the remaining reads and removing noise based on the structure of known variants; classifying the remaining reads by allele; and identifying protein truncating variants.

In some embodiments, the input sequencing data is classified by length to denoise the data based on the expected length of the gene. Read lengths are compared to the lengths of known alleles of the gene of interest. Reads lengths which are not consistent with that of a known allele are assumed to include errors in sequencing, such as sequencing-introduced insertions or deletions, and are denoised to create a first dataset that has removed reads with sequencing errors. Sequencing artifacts can be artifacts such as a repeated region in the sequencing read caused by an error in the sequencing reaction, the amplification reaction and/or an instrumentation error, causing the read to contain a DNA sequence structure that is not representative of the individual's actual genome. Reads whose length is consistent with those of known alleles are then used to create a first dataset.

In some embodiments, denoising of the input data may be accomplished by classifying the reads by length and removing lengths that are inconsistent with the length of known alleles of the gene, creating a first dataset of reads by removing said reads from the dataset. Reads are inconsistent with the length of known alleles of the gene if they are outside a range of lengths for alleles known to exist for the gene that is being genotyped. Thus, these reads are determined to include artifacts, and are excluded from the dataset as noise.

In some embodiments, denoising of the first dataset to create the second dataset may be accomplished by mapping references of the repeat sequences to each of the long-read sequencing reads, and creating a map of the structure for each read. The reference sequences are mapped using a software to determine the position of each repeat in the DNA sequence of the read, as well as the number of repeats in the read. Reads that display a structure that is inconsistent with known alleles of the gene are determined to include artifacts, and are excluded from the dataset as noise.

In some embodiments, mapping reference repeat sequences to the long-read sequencing reads may be accomplished through the use of a software such as BEDTools, as described in Aaron R. Quinlan, Ira M. Hall, BEDTools: a flexible suite of utilities for comparing genomic features, Bioinformatics, Volume 26, Issue 6, 15 Mar. 2010, Pages 841-842. BEDTools includes a variety of sequence analysis tools, such as intersect, merge, count, complement, and shuffle tools.

In some embodiments, denoising of the first sequencing dataset to create a second dataset may include the culling of reads from the dataset that are found to have inappropriate structure as artifacts. Reads structure may first be determined using a software tool such as BEDTools to map repeat sequences to the read. The number and position of the repeats is used as the structure of the read. Reads are culled as having "inappropriate structure" when the read includes either a combination of repeats or a sequence of repeats that does not exist in known alleles of the gene.

In some embodiments, the reads of the second dataset may be transformed into a third dataset of reads classified by allele, by correcting for PCR imbalance, determining the copy number of the individual, and removing read sets that are found to be noise.

PCR is often used for the preparation of a DNA sample for sequencing to assure that there are sufficient DNA sequences for assembly. After PCR, the ideal result would be a dataset that contained reads in the same proportion as the samples that existed prior to amplification. However, the mechanism of PCR creates an artificial imbalance that creates an over-abundance of shorter reads. PCR imbalance is the unavoidable consequence of the known fact that shorter sequences will be amplified at a faster rate than longer sequences in PCR. Thus, the results of PCR will always contain an artificially inflated quantity of smaller sequences compared to the quantity of longer sequences.

PCR imbalance is specifically problematic in heterogeneous alleles, where a shorter allele will be replicated at a higher rate, leading to an artificial imbalance in the ratio of sequences between the alleles.

In genes with repeat regions, an individual's alleles will often have different copy-numbers of repeat regions. Copy-number homogeneous ("CN-HOM") individuals will have the same number of repeats in both alleles. Copy-number heterogeneous ("CN-HET") individuals will have alleles with different numbers of repeats.

In CN-HET individuals, PCR-imbalance will cause their sequencing data to have an unbalanced proportion of reads corresponding to the allele with a smaller copy number, because this allele will be amplified at a greater frequency during PCR. Thus, instead of the approximately equal distribution of alleles in the sequencing data, the reads will often be imbalanced, with reads corresponding to the shorter allele being present in a significantly greater proportion than those of the longer allele.

In some embodiments, a computer system may capture and synthesize sequencing data, leveraging machine learning and/or artificial intelligence, to determine genotypes. The computer system may include any suitable data storage capabilities, such as cloud storage, to access and/or store any of the above data. In that way, the computer system may access and analyze historical and/or current (e.g., real-time or near real-time) data. In some embodiments, the computer system may include or be implemented via one or more local or remote processors, servers, transceivers, memory units, mobile devices, wearables, smart watches, smart contact lenses, smart glasses, augmented reality glasses, virtual reality headsets, mixed or extended reality glasses or headsets, voice or chat bots, AI bots (including generative AI bots), and/or other electronic or electrical components, which may be in wired or wireless communication with one another.

In the example embodiment, the computer system includes at least one computing device. The computing device is configured to perform the functions that may be more generally described herein as being performed by and/or attributed to the overall computer system.

In particular, in the example embodiment, the computing device may be in communication with one or more computing devices associated with a user. These computing devices may include a personal mobile computing device, such as a smart phone, tablet, and the like.

The computing device may receive portions of sequencing data, and/or any other type of data from alternative computing devices, such as sequencing devices. Additionally, or alternatively, the computing device may access portions of such data from one or more databases or other memory devices. The computing device may be configured to aggregate, combine, synthesize, parse, compare, and/or otherwise process this data, as described in more detail herein, in order to determine a genotype.

The computing device may store any received, retrieved, and/or accessed data in one or more databases, and may store the determined genotype and/or other generated data in the one or more databases. A database may be any suitable storage location, and may in some embodiments include a cloud storage device such that the database may be accessed by a plurality of computing devices (e.g., a plurality of user analytics computing devices, third-party computing devices, etc.). The database may be integral to the computing device or may be remotely located with respect thereto.

The technical effect of the systems and processes described herein may be achieved by performing at least one of the following steps: (i) receiving an input set of genetic sequencing data; (2) measuring at least one repeat structure of at least one sequence read of the genetic sequencing data and remove sequence reads with abnormal repeat structures to generate a first dataset, the first dataset excluding sequence reads with sequence artifacts; (3) filtering sequence reads of the first dataset to generate a second dataset, the second dataset excluding sequences with structural artifacts; (4) applying input data to a model to generate a third dataset, the input data comprising sequence reads of the second dataset, and the third dataset including sequencing reads categorized by allele; (5) generating a consensus sequence for each allele in the third dataset to generate a fourth dataset of consensus reads for all alleles in the third dataset; (6) translating each allele of the fourth dataset to generate a fifth dataset, the fifth dataset including the corresponding amino-acid sequence of each allele; and (7) determining a protein-altering variant status based on the amino-acid sequences of the fifth dataset. The protein-altering variant status may include whether a variant has an effect on protein structure and/or the effect the variant has on protein structure. For example, the protein-altering variant status may indicate the sequence includes protein truncating variants (PTVs or pLoFs) and/or the dosage of any PTVs (pLoF burden) observed.

At least one of the technical problems addressed by the systems and methods disclosed herein may include: (i) time-consuming, labor-intensive, and costly process for determining genotypes; (ii) limited data being leveraged in the determination of genotypes; (iii) limited qualitative and quantitative analysis of genotypes in the drug candidate selection process; and (iv) noise and systemic variation in the sequencing read data significantly impacting the accuracy and functionality in genotyping analysis.

The resulting technical effects may include, for example: (i) more accurate genotyping; (ii) ability to receive data from a plurality of different data sources and translating the data into a format for further analysis; (iii) reduced processing time and costs associated with genotyping; (iv) significant reduction of noise and systemic variation in sequencing read data; and (v) more accurate disease diagnosis.

Example computer systems for genotyping are disclosed herein. For example, FIG. 1 depicts a schematic diagram of an example computer system 100. Computer system 100 is configured to determine genotypes. In one embodiment, computer system 100 may include and/or facilitate communication between a genotyping computing device 110 and one or more user computing devices 130 (which may also be referred to as "mobile devices") and/or between genotyping computing device 110 and one or more of third-party devices 140 and/or genotyping servers 150.

Genotyping computing device 110 may be implemented as a server computing device with artificial intelligence and deep learning functionality. Alternatively, genotyping computing device 110 (and/or user computing devices 130) may be implemented as any device capable of interconnecting to the Internet, including mobile computing device or "mobile device," such as a smartphone, a "phablet," or other web-connectable equipment or mobile devices (such as one or more local or remote processors, servers, transceivers, memory units, mobile devices, wearables, smart watches, smart contact lenses, smart glasses, augmented reality glasses, virtual reality headsets, mixed or extended reality glasses or headsets, voice or chat bots, AI bots (including generative AI bots), and/or other electronic or electrical components, which may be in wired or wireless communication with one another).

Genotyping computing device 110 may be in communication with one or more user computing devices 130, third party devices 140, and/or genotyping server 150, such as via wireless communication or data transmission over one or more radio frequency links or wireless communication channels. In the example embodiment, components of computer system 100 may be communicatively coupled to the Internet through many interfaces including, but not limited to, at least one of a network, such as the Internet, a local area network (LAN), a wide area network (WAN), or an integrated services digital network (ISDN), a dial-up-connection, a digital subscriber line (DSL), a cellular telecommunications connection (e.g., a 3G, 4G, 5G, etc., connection), a cable modem, and a BLUETOOTH connection.

Computer system 100 also includes one or more database(s) 120 containing information on a variety of matters. For example, database 120 may include information such as sequencing data (e.g., long-read sequencing data) and/or any other information used, received, and/or generated by computer system 100 and/or any component thereof, including such information as described herein. In one embodiment, database 120 may include a cloud storage device, such that information stored thereon may be securely stored but still accessed by one or more components of computer system 100, such as, for example, genotyping computing device 110, user computing devices 130, and/or genotyping servers 150. In some embodiments, database 120 may be stored on genotyping computing device 110. In an alternative embodiment, database 120 may be stored remotely from genotyping computing device 110 and may be non-centralized.

In some embodiments, user computing devices 130 may include computers that include a web browser or a software application to enable user computing devices 130 to access the functionality of genotyping computing device 110 using the Internet or a direct connection, such as a cellular network connection. User computing devices 130 may be any device capable of accessing the Internet including, but not limited to, a desktop computer, a mobile device (e.g., a laptop computer, a personal digital assistant (PDA), a cellular phone, a smartphone, a tablet, a phablet, netbook, notebook, smart watches or bracelets, smart glasses, wearable electronics, pagers, virtual reality headsets, augmented reality glasses, voice or chat bots, wearables, etc.), or other web-based connectable equipment.

User computing devices 130 may be used to access a data management app 112 maintained by genotyping computing device 110, for example, via a user interface 132 when data management app 112 is executed on user computing device 130. A user may use data management app 112 to provide inputs to genotyping computing device 110, view genotypes determined by genotyping computing device 110, and perform other actions, including those described elsewhere herein.

Third party devices 140 may be computing devices associated with external sources of data. Genotyping computing device 110 may request, receive, and/or otherwise access data from third party devices 140. Third party devices 140 may be any devices capable of interconnecting to the Internet, including a server computing device, a mobile computing device or "mobile device," such as a smartphone, or other web-connectable equipment or mobile devices.

Figure 2:
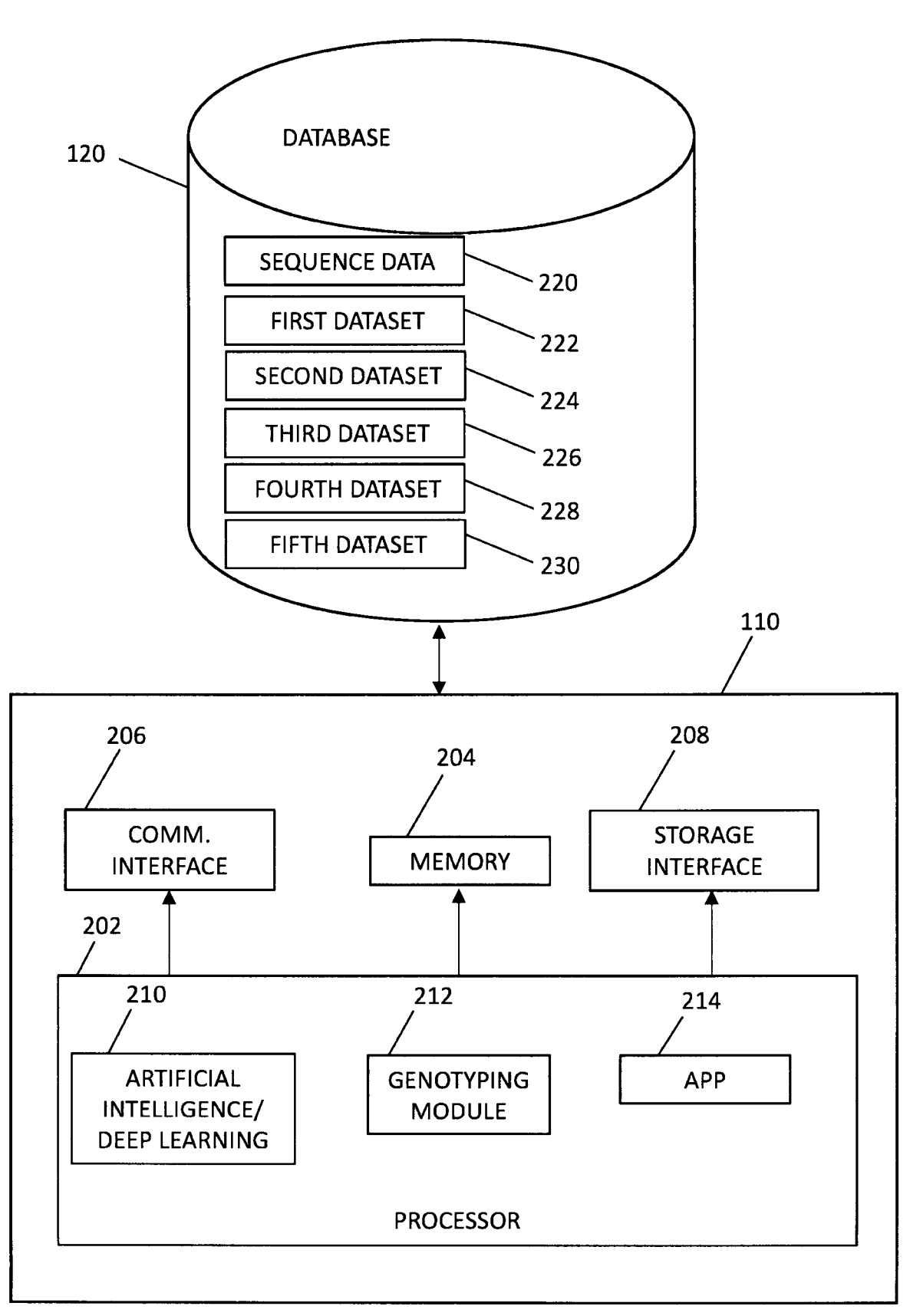
FIG. 2 illustrates a block diagram of an example genotyping computing device that may be used with the example computer system illustrated in FIG. 1.

Example user analytics computing devices are disclosed herein. For example, FIG. 2 depicts genotyping computing device 110 (as shown in FIG. 1), according to an embodiment. In some embodiments, genotyping computing device 110 may include a processor 202, a memory 204 (which may be similar to database 120, also shown in FIG. 1), a communication interface 206, and a storage interface 208. Processor 202 is configured to execute instructions, which may be stored in memory 204. Processor 202 includes one or more processing units (e.g., in a multi-core configuration) and may be configured to execute a plurality of modules.

In some embodiments, processor 202 is operable to execute an artificial intelligence/deep learning (AI/DL) module 210, a genotyping module 212, and a module 214 that maintains functionality for data management app 112 (shown in FIG. 1). Modules 210, 212, and 214 may include specialized instruction sets, and/or coprocessors. Database 120 and/or memory 204 may store any data and/or instructions necessary for modules 210, 212, and 214 to function as described herein. In the example embodiment, database 120 may store sequencing data (e.g., long-read sequencing data) 220, first datasets 222 (e.g., datasets excluding reads with sequence artifacts), second datasets 224 (e.g., datasets excluding sequences with structural artifacts), third datasets 226 (e.g., datasets including sequencing reads categorized by allele), fourth datasets 228 (e.g., datasets including consensus reads for each allele), fifth datasets 230 (e.g., datasets including the corresponding amino-acid sequence for each allele), and/or any other information used, received, and/or generated by genotyping computing device 110 (e.g., a sixth dataset of protein-truncating variants).

Figure 3:
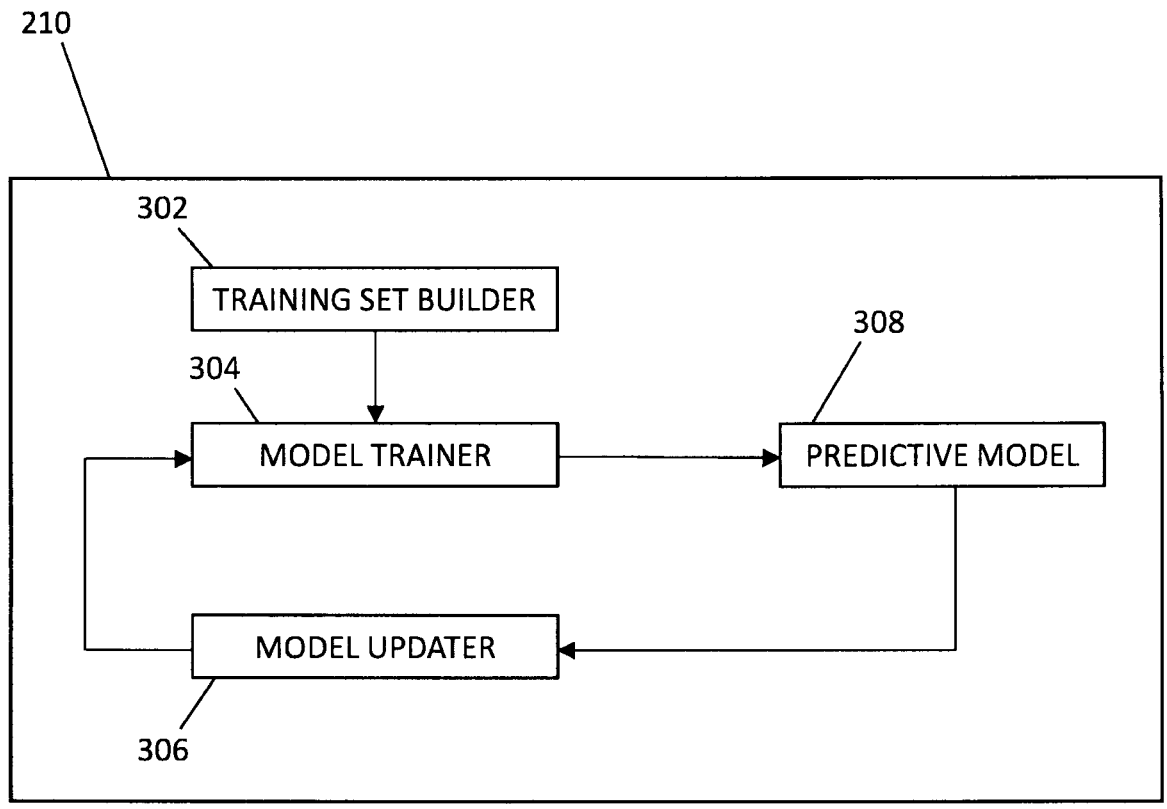
FIG. 3 illustrates a block diagram of an artificial intelligence (AI)/deep learning (DL) module that may be used with the genotyping computing device illustrated in FIG. 2.

AI/DL module 210 may execute artificial intelligence and/or deep learning functionality on behalf of genotyping module 212. Specifically, AI/DL module 210 may include any rules, algorithms, training data sets/programs, and/or any other suitable data and/or executable instructions that enable genotyping computing device 110 to employ artificial intelligence and/or deep learning to determine genotypes. FIG. 3 depicts an AI/DL module 210 (as shown in FIG. 2), according to an embodiment. In some embodiments, AI/DL module 210 includes a training set builder module 302 programmed to submit one or more queries to database 120 (shown in FIGS. 1 and 2) to retrieve data and/or subsets of data, and to use those subsets of data to build training data sets for generating predictive model 308.

In example embodiments, training set builder module 302 is programmed to retrieve training data sets from the retrieved subsets of data. Each training data set corresponds to historical data, which may include one or more second datasets 224 (e.g., datasets excluding sequences with structural artifacts) and/or any other information used, received, and/or generated by genotyping computing device 110, and the corresponding allele classification which was previously determined, as opposed to completed in real-time with respect to the time of retrieval by training set builder module 302. Each training data set can include model input data along with result data representing an allele classification. The model input data can represent factors that may be expected to, or unexpectedly be found during model training to, have some correlation with the allele classification. In some embodiments, the model input data may comprise one or more second datasets 224 (e.g., datasets excluding sequences with structural artifacts) and/or any other information used, received, and/or generated by genotyping computing device 110.

After training set builder module 302 generates training data sets, it passes the training data sets to model trainer module 304, which is programmed to apply the model input data fields of each training data set as inputs to one or more machine learning models. Each of the one or more machine learning models is programmed to produce, for each training data set, at least one output intended to correspond to, or "predict," a value of the at least one result data field of the training data set. Machine learning techniques may be used to train the model to identify and recognize patterns in existing data in order to facilitate making predictions for subsequent new input data. For example, support vector machines (SVM), neural networks, and multilayer perceptron (MLP) classifiers may be used to train and optimize the model.

Model trainer module 304 is programmed to compare, for each training data set, the at least one output of the model to the at least one result data field of the training data set, and apply a machine learning algorithm to adjust parameters of the model in order to reduce the difference or "error" between the at least one output and the corresponding at least one result data field. In this way, model trainer module 304 trains the machine learning model to accurately determine allele classification. In other words, model trainer module 304 cycles the one or more machine learning models through the training data sets, causing adjustments in the model parameters, until the error between the at least one output and a previously determined allele classification falls below a suitable threshold, and then uploads at least one trained machine learning model to predictive model module 308 for application to new sequencing data. For example, model trainer module 304 may be programmed to compare, for each training data set, an allele classification as determined by the model to an allele classification as previously determined using traditional testing methods. Model trainer module 304 may then adjust one or more weight values using a machine learning algorithm, such as a backpropagation algorithm, in order to reduce the difference between the allele classification as determined by the model and the allele classification as determined using traditional testing methods.

In some embodiments, the one or more machine learning models may include one or more neural networks, such as a convolutional neural network, a deep learning neural network, or the like. The neural network may have one or more layers of nodes, and the model parameters adjusted during training may be respective weight values applied to one or more inputs to each node to produce a node output. In other words, the nodes in each layer may receive one or more inputs and apply a weight to each input to generate a node output. The node inputs to the first layer may correspond to the model input data fields and the node outputs of the final layer may correspond to the at least one output of the model, intended to predict the at least one result data field. For example, the node inputs to the first layer may correspond to sequencing data (e.g., long-read sequencing data) and the node outputs of the final layer may correspond to at least one allele classification. One or more intermediate layers of nodes may be connected between the nodes of the first layer and the nodes of the final layer. As model trainer module 304 cycles through the training data sets, model trainer module 304 applies a suitable backpropagation algorithm to adjust the weights in each node layer to minimize the error between the at least one output (e.g., an allele classification as determined by the model) and the corresponding result data field (e.g., the previously determined allele classification). In this fashion, the machine learning model is trained to produce one or more outputs which reliably determines allele classifications. Alternatively, the machine learning model has any suitable structure. In some embodiments, model trainer module 304 provides an advantage by automatically discovering and properly weighting complex, second- or third-order, and/or otherwise nonlinear interconnections between the model input data fields and the at least one output. Absent the machine learning model, such connections are unexpected and/or undiscoverable by human analysts.

Additionally, or alternatively, the one or more machine learning models may include one or more multilayer perceptron (MLP) classifiers. An MLP classifier may comprise input and output layers, and one or more hidden layers with many neurons stacked together. For example, an MLP classifier in accordance with the present disclosure may comprise an input layer comprising sequencing data and an output layer comprising an allele classification.

Additionally, or alternatively, the one or more machine learning models may include one or more support vector machines (SVMs). SVMs are supervised learning models with associated learning algorithms that analyze data for classification and regression analysis. More particularly, an SVM constructs a hyperplane or set of hyperplanes in a high or infinite-dimensional space, which can be used for classification, regression, or other tasks like outlier detection. For example, in some embodiments, training data sets may each be marked as belonging to one of two categories based on the previously determined allele classification. The SVM maps training data sets to points in space so as to maximize the width of the gap between the two categories. New data sets are then mapped into that same space and predicted to belong to a category based on which side of the gap they fall.

In some embodiments, predictive model module 308 compares the known allele classification with the output from the trained model, and routes the comparison result to a model updater module 306 of AI/DL module 210. Model update module 306 is programmed to derive a correction signal from the comparison results, and to provide correction signal to model trainer module 304 to enable updating or "re-training" of the at least one machine learning model to improve performance. For example, one or more new weight values may be derived from the comparison results, and the correction signal may adjust weight values applied to one or more inputs. The retrained machine learning model may be periodically re-uploaded to predictive model module 308.

In some embodiments, model trainer module 304 may update the training dataset by creating one or more new historical records which includes new data and re-training the operator model using the updated training dataset, further improving the accuracy of the operator model.

Genotyping module 212 may employ AI/DL module 210 to use the trained model to determine an allele classification. More particularly, genotyping module 212 may use the output from the trained model to determine an allele classification. The determined allele classification and other data may be viewable via data management app 112.

App module 214 is configured to facilitate maintaining data management app 112 and providing the functionality thereof to users. App module 214 may store instructions that enable the download and/or execution of data management app 112 at user computing devices 130. App module 214 may store instructions regarding user interfaces, controls, commands, settings, and the like, and may format data into a format suitable for transmitting to user computing devices 130 for display thereof.

In some embodiments, processor 202 is operatively coupled to communication interface 206 such that genotyping computing device 110 is capable of communicating with remote device(s) such as user computing devices 130, third party devices 140, and/or genotyping on servers 150 (all shown in FIG. 1) over a wired or wireless connection. For example, communication interface 206 may receive sequencing data (e.g., long-read sequencing data) user computing devices 130, and/or third-party devices 140. Communication interface 206 may include, for example, a wired or wireless network adapter and/or a wireless data transceiver for use with a mobile telecommunications network.

Processor 206 may also be operatively coupled to database 120 (and/or any other storage device) via storage interface 208. Database 120 may be any computer-operated hardware suitable for storing and/or retrieving data. In some embodiments, database 120 may be integrated in genotyping computing device 110. For example, genotyping computing device 110 may include one or more hard disk drives as database 120. In other embodiments, database 120 is external to genotyping computing device 110 and is accessed by a plurality of computer devices. For example, database 120 may include a storage area network (SAN), a network attached storage (NAS) system, multiple storage units such as hard disks and/or solid-state disks in a redundant array of inexpensive disks (RAID) configuration, cloud storage devices, and/or any other suitable storage device.

Storage interface 208 may be any component capable of providing processor 202 with access to database 120. Storage interface 208 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 202 with access to database 120.

Processor 202 may execute computer-executable instructions for implementing aspects of the disclosure. In some embodiments, processor 202 may be transformed into a special purpose microprocessor by executing computer-executable instructions or by otherwise being programmed. For example, processor 202 may be programmed with the instructions such as those illustrated in FIG. 26.

Memory 204 may include, but is not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are example only, and are thus not limiting as to the types of memory usable for storage of a computer program.

Specific embodiments of the method disclosed herein may be utilized to genotype the filaggrin gene.

Filaggrin is a highly charged, cationic protein that aids aggregation and subsequent disulfide bonding of keratin filaments. It is derived from profilaggrin, a large (4400 kD) phosphorylated precursor expressed as keratohyalin granules in the granular layer of the epidermis. During the transition from the granular layer to the stratum corneum, profilaggrin is converted to filaggrin by site-specific proteolysis and dephosphorylation. In addition to profilaggrin processing to filaggrin, the transition from a granular cell to a corneocyte is characterized by the degradation of the nucleus and other organelles, assembly of a cornified envelope, and reorganization of the keratin intermediate filament network into a two-dimensional sheet.

Filaggrin plays a critical role in the generation and maintenance of a flexible and hydrated stratum corneum and its hydrolysis is carefully regulated to generate free amino acids that form a major part of the natural moisturizing factors (NMF). The transition from a granular precursor, profilaggrin, to a diffusely distributed protein, happens quickly at the granular to stratum corneum transition in response to an initiating signal which is not yet known. That profilaggrin is expressed as a precursor, rather than a mature protein, suggests that filaggrin expression must be regulated to prevent cytotoxic effects.

Many inflammatory skin conditions are characterized by attenuation of the granular layer with concomitant parakeratosis, e.g. retained nuclei in the keratinocytes of the stratum corneum. While the signals that are disrupting terminal differentiation in these inflammatory conditions may be disparate, a common final theme is loss of the granular layer with subsequent incomplete terminal differentiation. In conditions where profilaggrin is decreased, such as atopic dermatitis, or essentially absent, as in ichthyosis vulgaris, the quality of the stratum corneum is compromised due to the inability of an NMF-depleted stratum corneum to remain hydrated under the desiccating action of the environment.

Filaggrin is a filament-associated protein that plays an important role in the skin. Recently, Loss of Function mutations in Filaggrin have been correlated with several skin conditions such as ichthyosis vulgaris, atopic eczema, asthma, and other allergies.

Figure 4:
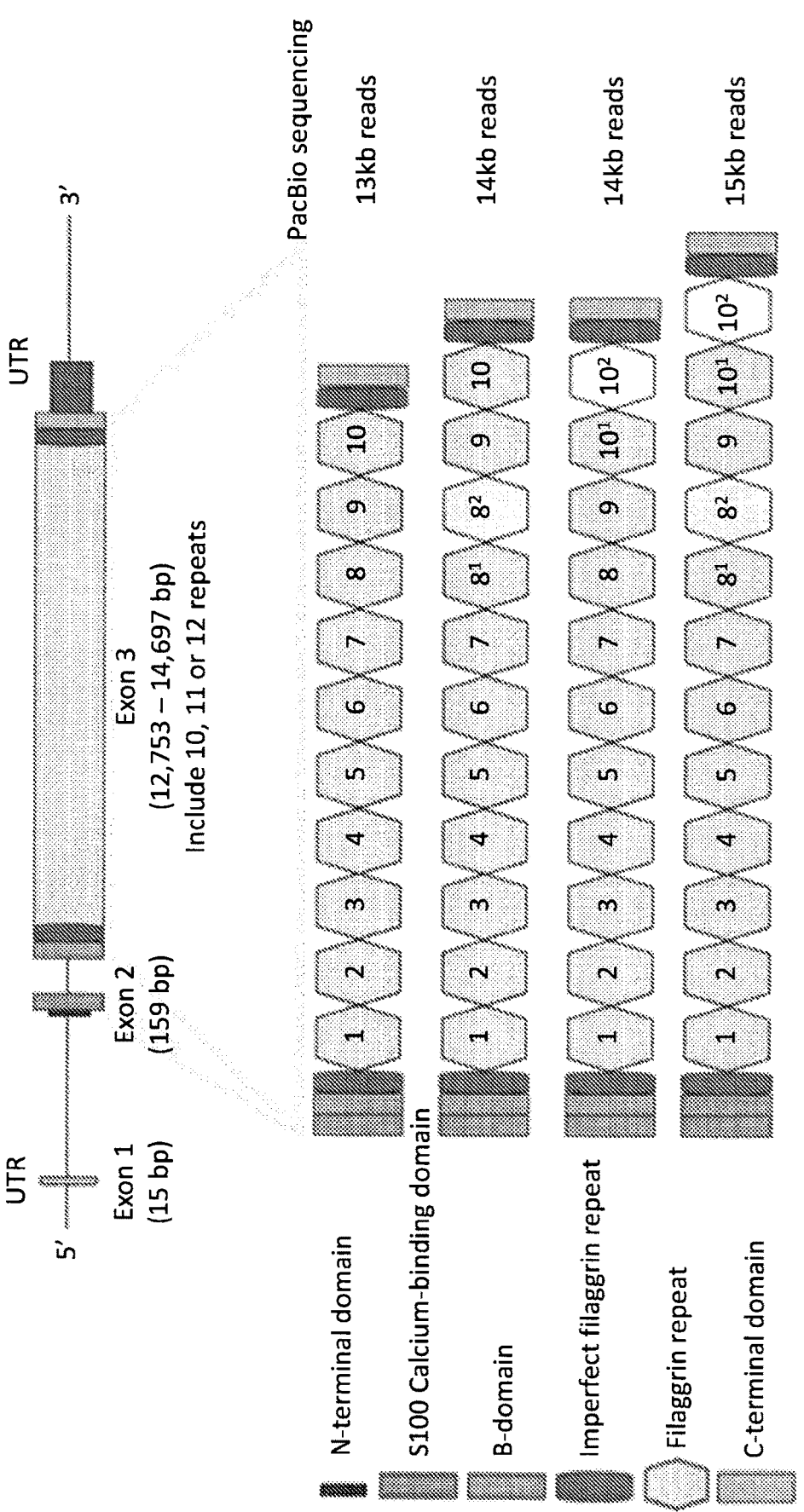
FIG. 4 is a schematic diagram showing the structure of the Filaggrin (FLG) gene.

As depicted in FIG. 4, Filaggrin is made up of three exons. Filaggrin is a repeat rich gene, with 10 to 12 complete repeats in the third exon of the gene. The length of each repeat is between 972 and 975 nucleotides.

FIG. 4 further depicts the variable length of Filaggrin's third exon. Filaggrin's third exon varies in length from 12,753 to 14,697 reads, depending on the genotype of the individual. Currently, as known in the art, Filaggrin alleles are found in four genotypes including 10, 11, or 12 repeats in Exon 3.

Figure 5:
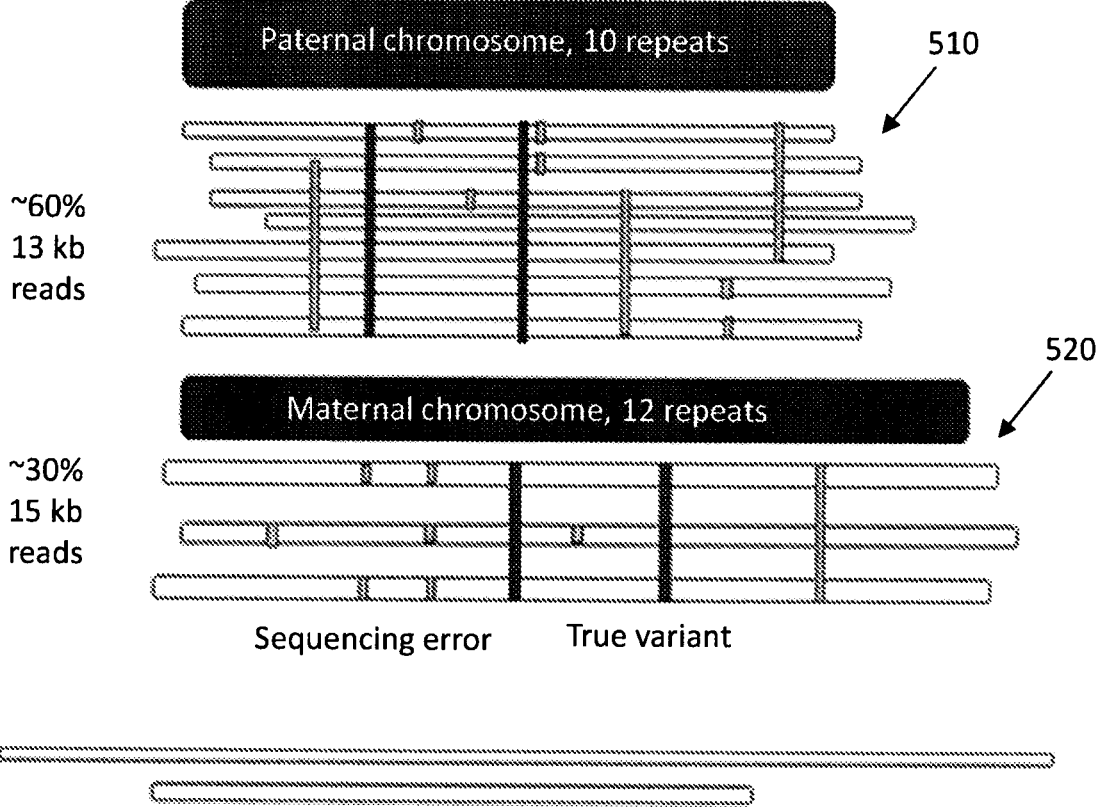
FIG. 5 is a schematic diagram of PCR bias observed after amplification of haplotypes.

FIG. 5 depicts PCR bias in a sequencing dataset of a CN-HET individual. The paternal chromosome 510 allele shows a copy number of 10 and an average read length of 13,000 nucleotides, and the maternal chromosome allele 520 shows a copy number of 12 and an average read length of 15,000 nucleotides. Due to PCR bias, the individual's sequencing data contains approximately 60% of reads corresponding to the shorter paternal chromosome allele 510, while the longer maternal chromosome 520 allele only appears in approximately 30% of the data.

Figure 6:
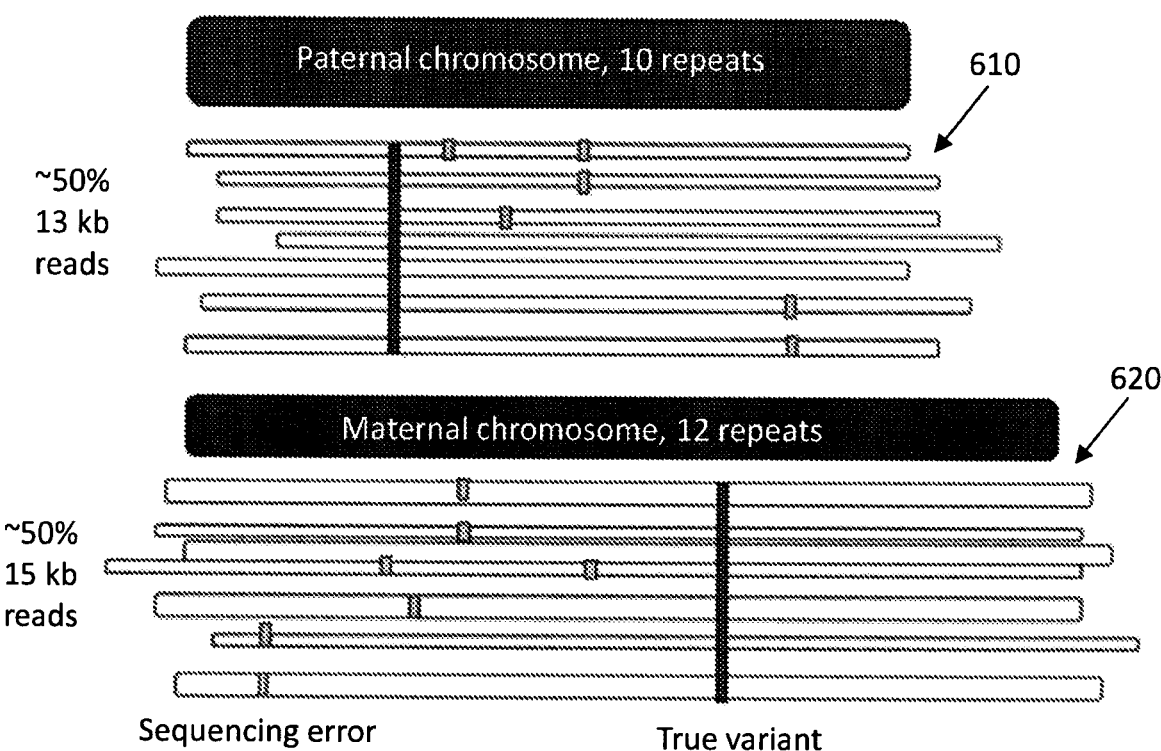
FIG. 6 is a schematic diagram illustrating PCR amplification of haplotypes.

FIG. 6 depicts PCR amplification of haplotypes in an example dataset of a CN-HET individual showing the target read length with equal distribution. The copy number of the paternal chromosome 610 allele for the 10 repeats at 13 kb reads is amplified equally to the maternal chromosome 620 or larger repeat (12 repeats) of 15 kb reads. No artifacts would be observed after alignment of the sequencing data from PacBio.

Due to the mechanism of amplification of DNA fragments in PCR, if the difference in copy number is significant, the PCR imbalance will be greater, because a logarithmic increase is observed in the amplification of smaller samples in comparison to longer samples. To accurately genotype these individuals, the data may need to be adjusted to appropriately capture the genotype.

In FLG, since each repeat is about 1 kb in length, differences in copy number of only one can still cause a significant increase in the imbalance because of the size of the increase. For 5 example, due to each repeat of the FLG gene being approximately 1 kb, a difference in one repeat can have a great impact on the amplification imbalance observed.

In some embodiments, the reads of the second dataset can be adjusted for PCR imbalance by indexing the sequencing reads into unique groups by sequence structure, and analyzing the most frequent groups, to create a third dataset of reads that identify the alleles of the individual. Reads are categorized by structure into groups, and ordered by their frequency in the dataset. The reads in the most frequent group of reads (the "first frequent group") and, if existing, the second most frequent group of reads (the "second frequent group") are analyzed to categorize the samples as CN-HOM or CN-HET. If the reads segregate into only one frequency group of the copy number and structure, the sample is determined to be CN-HOM, and only the first frequent group is indexed as the individual's alleles. If the reads segregate into two or more frequency groups, the two largest frequency groups are analyzed for sequencing noise.

In some embodiments, the two largest frequency groups may be of the same copy number, but different structures. The ratio of their frequency can be compared. If the ratio is near 1, the individual is classified as CN-HET and both the first and second frequent groups are indexed and maintained in the third dataset. If the ratio is greater than one, the individual is classified as CN-HOM and only first frequent group is indexed and maintained for inclusion in the third dataset.

In some embodiments, reads in the second dataset are analyzed for sequencing noise via an analysis of their frequency. Reads are categorized into groups by structure, and ordered by their frequency in the dataset. The reads in the most frequent group of reads (the "first frequent group") and second most frequent group of reads (the "second frequent group") are identified. A null distribution is developed for the level of PCR-bias based on the difference in length between the first and second frequent groups. The distribution of the frequencies between the first and second frequent groups is then plotted on a logarithmic scale. Samples whose plots indicate an outlier from the expected frequency distribution are classified as CN-HOM, while those whose frequency distribution is in line with the expected distribution are classified as CN-HET. For CN-HOM samples, only the first frequent group is indexed and maintained in the third dataset. For CN-HET samples, both the first and second frequent groups are index and maintained in the third dataset.

In some embodiments, reads in the second dataset are analyzed for sequencing noise via an analysis of their copy number. If the copy number of the second frequent group is larger than the first frequent group, the individual is determined to be CN-HET, and the first and second frequent groups are indexed as the alleles of the individual. If the copy number of the second frequent group is smaller than the first frequent group, the individual is determined to be CN-HOM, and only the first frequent group is indexed as the individual's alleles.

In some embodiments, the transformation of the second to third dataset includes categorizing the samples as either copy number heterogeneous ("CN-HET") or copy number homogeneous ("CN-HOM") based on frequency ratio of the first and second most common read groups. If the frequency ratio is greater than expected, the reads are categorized as CN-HOM. This is because it is likely that reads of the second frequency group are likely sequencing artifacts when the frequency of the second frequent group is significantly lower than that of the first frequent group. If the frequency ratio is approximately as expected, they are marked as CN-HET. This is because both read groups are observed at higher frequencies than would be expected if one of the read groups was comprised of sequencing artifacts. If the first common read group is longer than that of the second, the sample is categorized based on whether the length of the first group is greater or less than that of the third group.

For example, sequencing reads, which may have been filtered to remove sequencing and/or structural artifacts, as described above, may then be classified by allele. This may be done by: (i) mapping sequences from known references of one or more individual repeats to the sequencing reads to determine the structure of the reads; (ii) grouping reads according to their structure; (iii) ordering the groups by frequency of the reads; (iv) identifying a first frequent group and, if existing, a second frequent group of reads; and/or (v) categorizing the individual as CN-HOM or CN-HET based on the differences in length of the first and second frequent groups, and/or frequency of each group in the dataset. The length may comprise a full length of the gene or copy numbers (i.e., number of repeat exons).

Categorizing the individual as CN-HOM or CN-HET in step (v) above may be accomplished by applying one or more of the following rules (1)-(5): (1) If the reads segregate into only one frequency group of the copy number and structure, the sample is determined to be CN-HOM. (2) Comparing the frequency of the reads in each group and if the frequency ratio is greater than predicted, the reads are categorized as CN-HOM. If the frequency ratio is in line with the predicted ratio, the reads are categorized as CN-HET. Distribution of frequencies may be calculated as set out above, based on analysis of the PCR bias. For example, a null distribution is developed for the level of PCR-bias based on the difference in length between the first and second frequent groups. The distribution of the frequencies between the first and second frequent groups is then plotted on a logarithmic scale. Samples whose plots indicate an outlier from the expected frequency distribution are classified as CN-HOM, while those whose frequency distribution is in line with the expected distribution are classified as CN-HET. (3) If the copy number of the second frequent group is smaller than the first frequent group, the individual is determined to be CN-HOM. (4) The copy number of the second frequent group is larger than the first frequent group, the individual is determined to be CN-HET. The foregoing Rules (1)-(5) may be performed by a trained or untrained model. For example, in some embodiments, Rules (1)-(5) may be done by an untrained classification model. Where the model is a trained model, the training data may comprise reads which have been filtered to remove sequencing or structural artifacts as described above to form the second dataset. The output for the training is the allele classification. That is, for CN-HOM allele classification is by heterozygous SNP and/or indel assignment to an allele. For CN-HET allele classification, this assigns allele by copy number.

In some embodiments, reads that have been classified as CN-HOM are further analyzed to determine the alleles of the individual. Reads of the first frequent group are aligned against a customized reference to detect heterozygous SNPs and Indels. Reads of the first frequency group are then separated into groups for each allele using a k-means clustering algorithm, as described in Lu, Y., Lu, S., Fotouhi, F. et al. Incremental genetic K-means algorithm and its application in gene expression data analysis. BMC Bioinformatics 5, 172 (2004). https://doi.org/10.1186/1471-2105-5-172.

Figure 7:
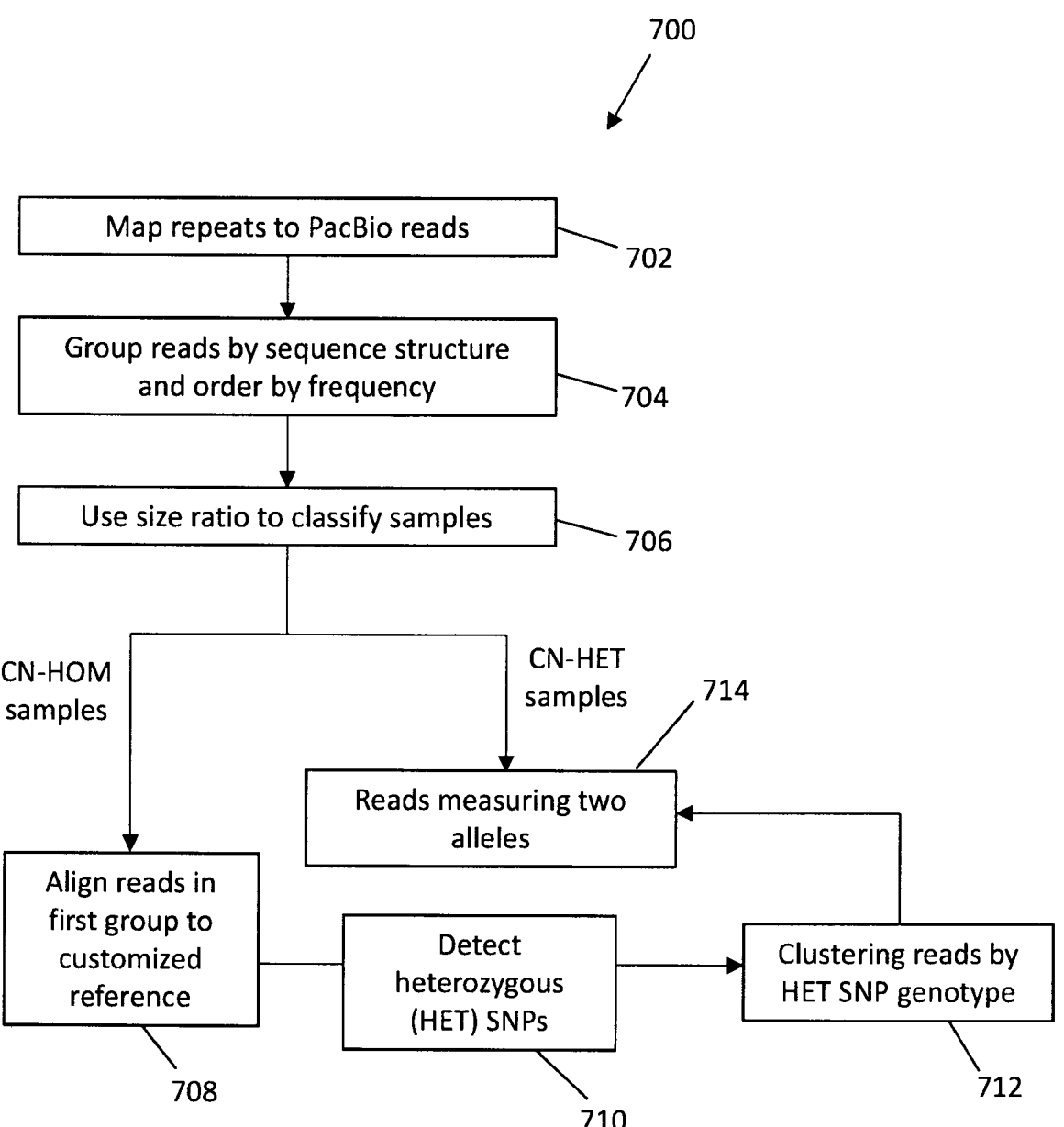
FIG. 7 is a flow diagram for mapping the repeats obtained after sequencing with PacBio through reads measuring two alleles.

FIG. 7 depicts a flowchart of a process for the transformation of the second to third dataset 700, according to an embodiment. First, at 702, reference sequences of each individual repeat are mapped to the reads of the second dataset, to generate a structure of each individual read, based on the repeats included in the read, and their order. At 704, the reads are grouped by sequence structure, and ordered by frequency. That is, reads that depict the same sequence structure are grouped together, and then each group is order by the percentage of total reads in which that structure appears. Reads are then classified as CN-HOM or CN-HET based on the size ratio of the first and second most common read groups at 706. Samples that are determined to be CN-HOM take the first frequent group and align them to a customized reference to further classify the reads into reads for each allele at 708. The reads may be classified into reads for each allele via an AI/ML model. In further embodiments, the AI/ML model comprises a single-step classifier and/or a multi-step classifier. In some embodiments, the AI/ML model includes a k-means clustering algorithm. The samples are analyzed for heterozygous SNPs at 710. These SNPs are then used to cluster the reads into alleles, based on their heterozygous SNP genotype at 712. The final output of this framework is the third dataset of reads categorized for each allele, either taken from the first and second frequent groups in CN-HET individuals, or from the clusters determined by the SNP genotype for CN-HOM individuals, as depicted in 714.

In some embodiments, the third dataset is further transformed to a fourth dataset by generating a consensus sequence for each of the alleles of the third dataset.

In some embodiments, the transformation of the third dataset to a fourth dataset may include generating a consensus sequence across each allele of the third dataset. The generation of the consensus sequence may be accomplished through the use of a software such as SPOA, as described in Vaser R, Sović I, Nagarajan N, Šikić M. Fast and accurate de novo genome assembly from long uncorrected reads. Genome Res. 2017 May; 27(5):737-746. Epub 2017 Jan. 18.

In some embodiments, the consensus sequence of the fourth dataset may be aligned to a customized reference to identify all nucleic acid changes. The sequence of the consensus sequence can be mapped to a reference sequence of the gene of interest, and variant nucleotides between the reference and the consensus sequence can be identified and further analyzed to detect their effect on the codons.

In some embodiments, the consensus sequence of the fourth dataset may be further transformed into a fifth dataset by translating the consensus sequence into the corresponding amino acid code.

In some embodiments, the fourth dataset is transformed into the corresponding amino acid code via the longest open reading frame ("ORF"), using a software program such as the getorf utility in the EMBOSS package, as described in EMBOSS: The European Molecular Biology Open Software Suite (2000), Rice, P. Longden, I. and Bleasby, A. Trends in Genetics 16, (6) pp 276-277. The getorf utility in the EMBOSS package can determine the longest open reading frame in the consensus sequence by determining the positions of start codons in the consensus sequence and determine which start codon would result in the longest reading frame.

Figure 8:
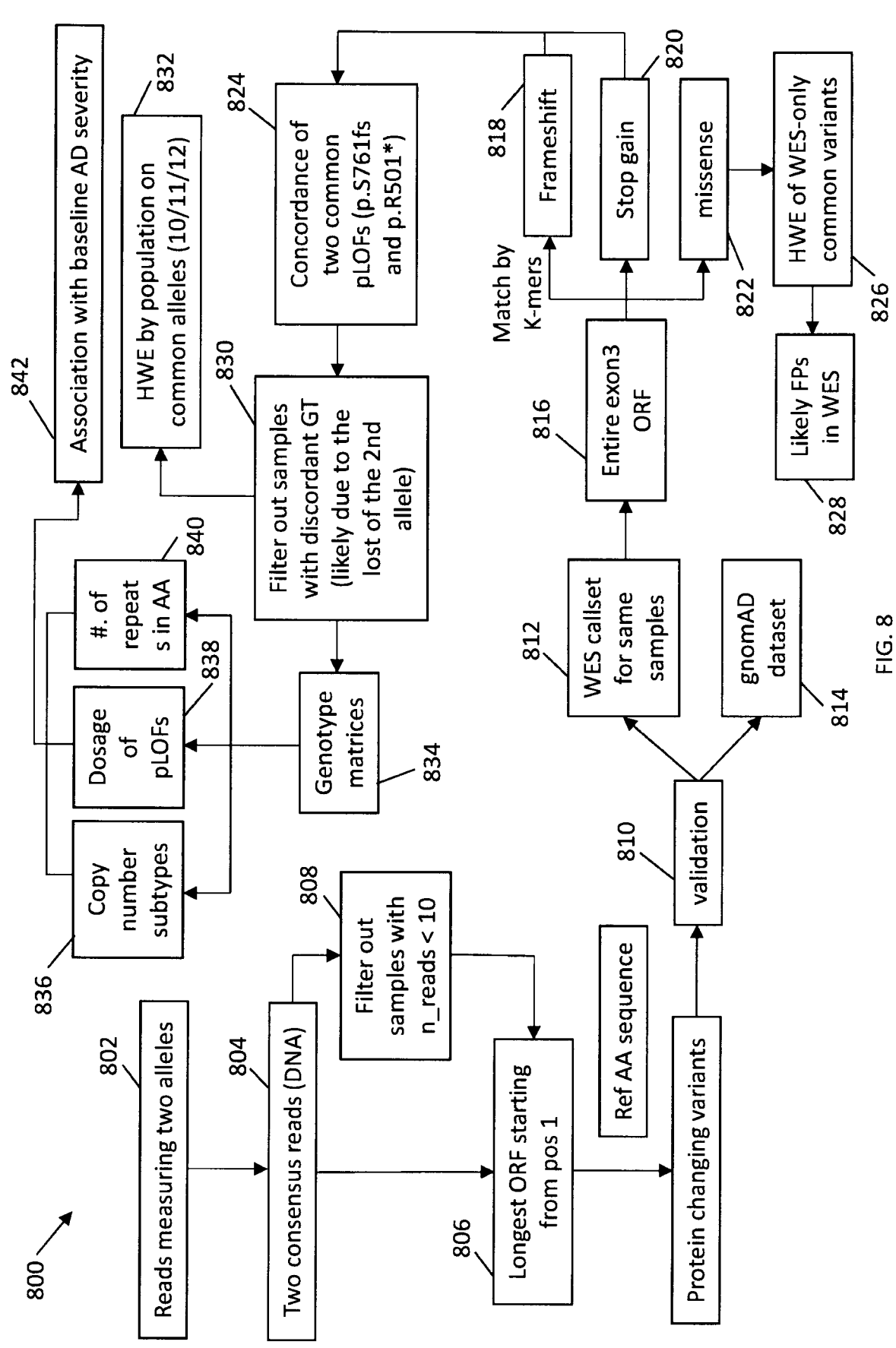
FIG. 8 is a flow diagram of the workflow from identification of reads measuring two alleles through association with baseline Atopic dermatitis (AD) severity and performing validation analyses such as Hardy Weinberg Equation (HWE) on common alleles.

FIG. 8 depicts a flow chart of a process for analyzing protein truncating variants for Atopic Dermatitis ("AD")

identified in the reference amino acid sequence 800, according to an embodiment. The process starts with identifying reads separated into two alleles at 802. Consensus sequences for the reads of each group are created at 804. Open Reading Frames ("ORF") are then evaluated, and the longest ORF is selected from position 1 and each allele is translated into its corresponding amino acid sequence at 806. Samples that have less than 10 reads are filtered out in this process at 808. The amino acid sequences are then evaluated against a reference amino acid sequence, and protein changing variants are identified at 808. Protein truncating variants are validated at 810 through two methods: (1) via an internal Whole Exome Sequencing ("WES") at 812, and (2) via an external database such as gnomAD, (See Karczewski et al., 2020), a genetics dataset including the exome and genome sequencing data of 141,456 multi-ethnic individuals, at 814.

For the WES validation, the callsets are further analyzed based on the entire exon3 ORF at 816. Protein changing variants from this set are evaluated based on the type of mutation, such as frameshift at 818, stop gain at 820, or missense at 822. Frameshift and stop gain mutations are pushed forward for concordance of common potential Loss of Function mutations ("pLoFs"), at 824. Missense mutations are analyzed based on a Hardy Weinberg Equation (HWE) analysis with common variants at 826, and marked as likely false. Encompassed in this process is filtering reads with less than 10 repeat units, aligning the largest ORF, interpretation of the DNA sequence into amino acid sequence and validation of the variants. Validation includes harmonizing the sequencing data of the variants, evaluating by HWE, and association with clinical traits, according to one embodiment.

The exon 3 ORF is analyzed and the changes in amino acid code are classified as frameshift, stop gain, or missense mutations. Missense mutations are analyzed via the Hardy-Weinberg Equation and then flagged as likely false positives at 828. Stop gain and frameshift mutations are analyzed after checking the concordance with common pLoF mutations at 824. Samples with discordant genotype ("GT") of the two common pLoFs are then further filtered at 830. The structural genotype was validated by checking the HWE of the common alleles at 832. Then the structural variants and PTVs are combined as a genotype matrix, as depicted in 834. The samples are then analyzed by copy number subtype 836, dosage of pLoFs 838, and the number of repeats in the amino acid sequence 840 in terms of their associated AD severity 842.

Figure 9:
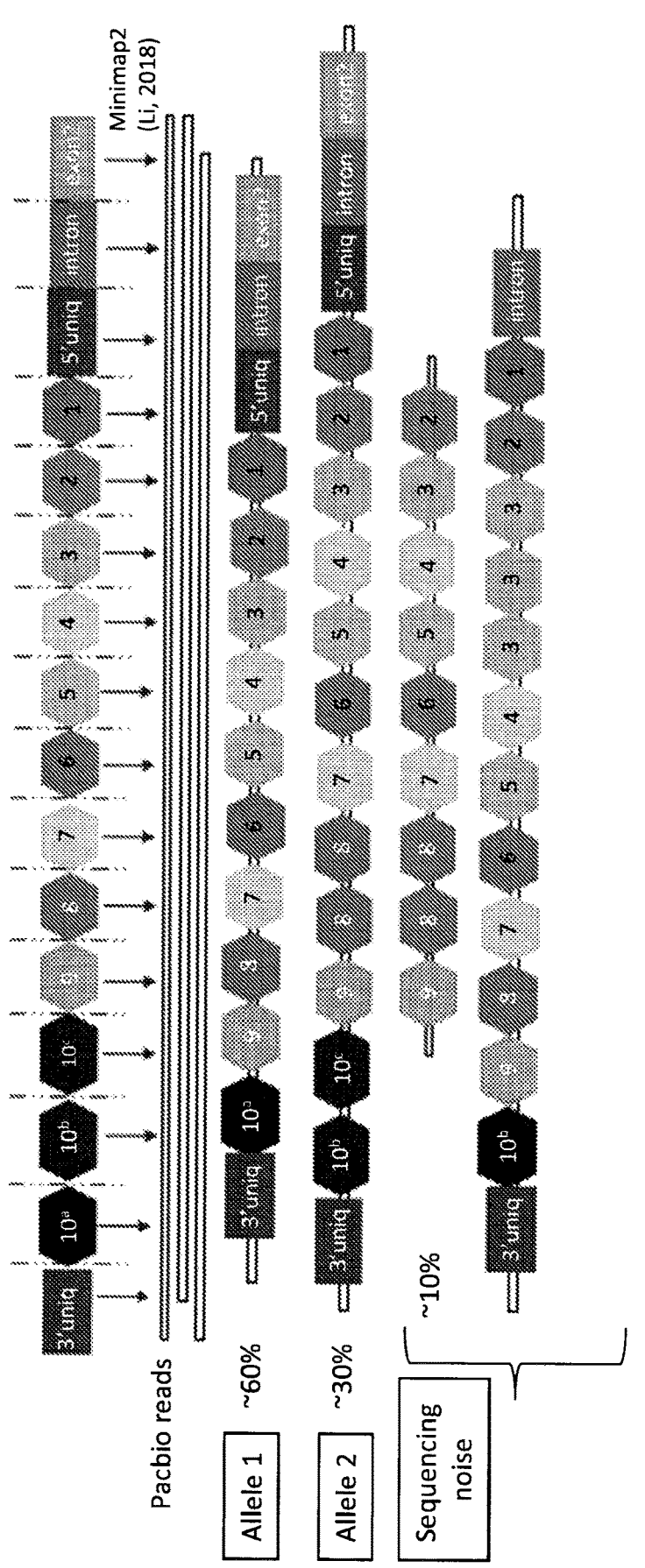
FIG. 9 is a schematic diagram illustrating utilizing the sequence structure of the repeats in order to filter out the sequencing noise from the true variants in accordance with an embodiment of the present disclosure.

FIG. 9 is a diagram depicting an example analysis of the sequence structure of the repeats to filter out sequencing noise from informative reads. Sequences for exon 2, intron and the 5' unique region, and the 3' unique region are used to identify sequencing artifacts, according to an embodiment. As depicted in FIG. 9, reads that lack structural features that are found in known references, such as the 5' and 3' unique regions, are excluded as noise. Similarly, reads that contain structural features that are not consistent with known variants, such as the triple repeat of repeat 3 in the lowest read shown in FIG. 9, are discarded as noise.

Figure 10:
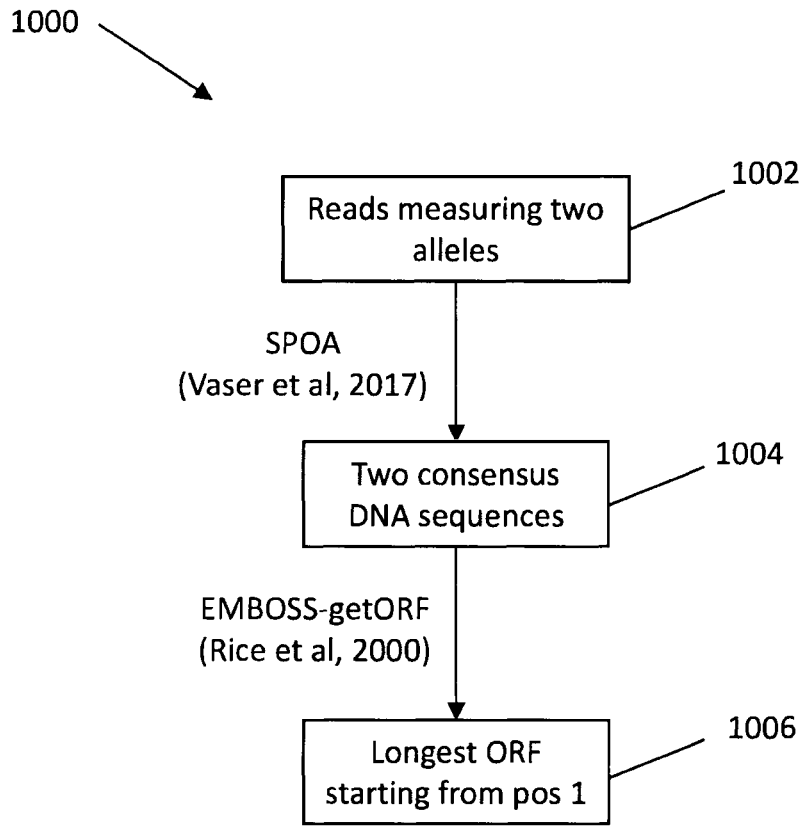
FIG. 10 shows the generation of two consensus sequences followed by the identification of the longest Open Reading Frames (ORF) were translated into amino acids, in accordance with an embodiment of the present disclosure.

FIG. 10 depicts a flowchart showing a process for identifying protein-truncating variants in the dataset 1000, according to an embodiment. The dataset begins with reads measuring two alleles at 1002. The reads measuring two alleles are translated into consensus DNA sequences via a software program such as SPOA, to generate a new dataset of consensus sequences for each allele at 1004. Then, ORF are identified in the consensus sequence using a software tool such as the getorf program in the EMBOSS software

US 12,682,982 B2

Figure 11:
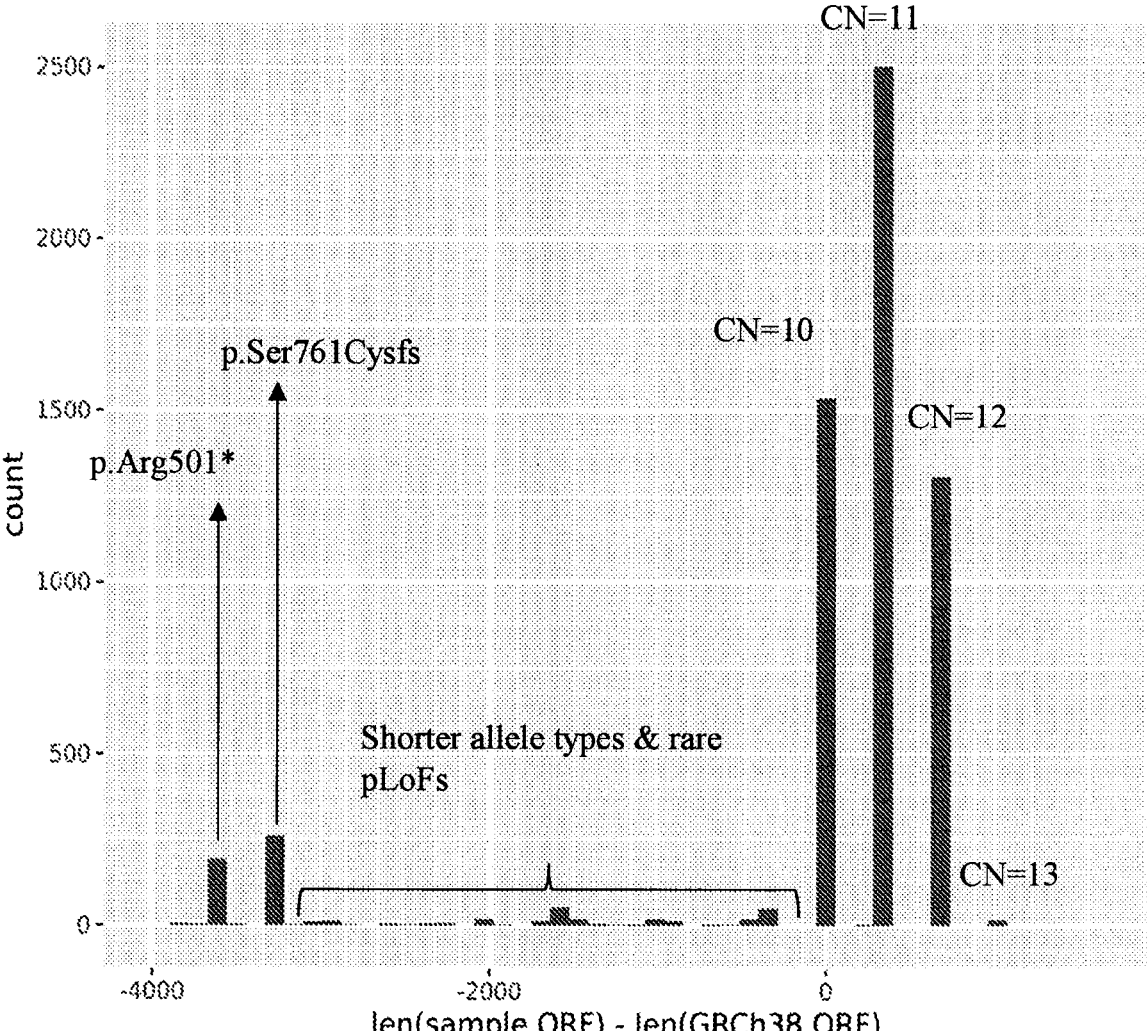
FIG. 11 shows the ORF length differences of detected haplotypes compared to the CN=10 allele (the GRCh38 reference allele) and was plotted against the frequency observed, in accordance with an embodiment of the present disclosure.

23 suite, to create a dataset of the longest ORF from starting position 1 at 1006. FIG. 11 depicts a graph showing the differences in value from the length of the generated ORFs, for Filaggrin data, according to an embodiment. The graph indicates both full protein lengths, as well as known variants that are correlated with disease, and rare variants that indicate a pLoF mutation.

Figure 12:
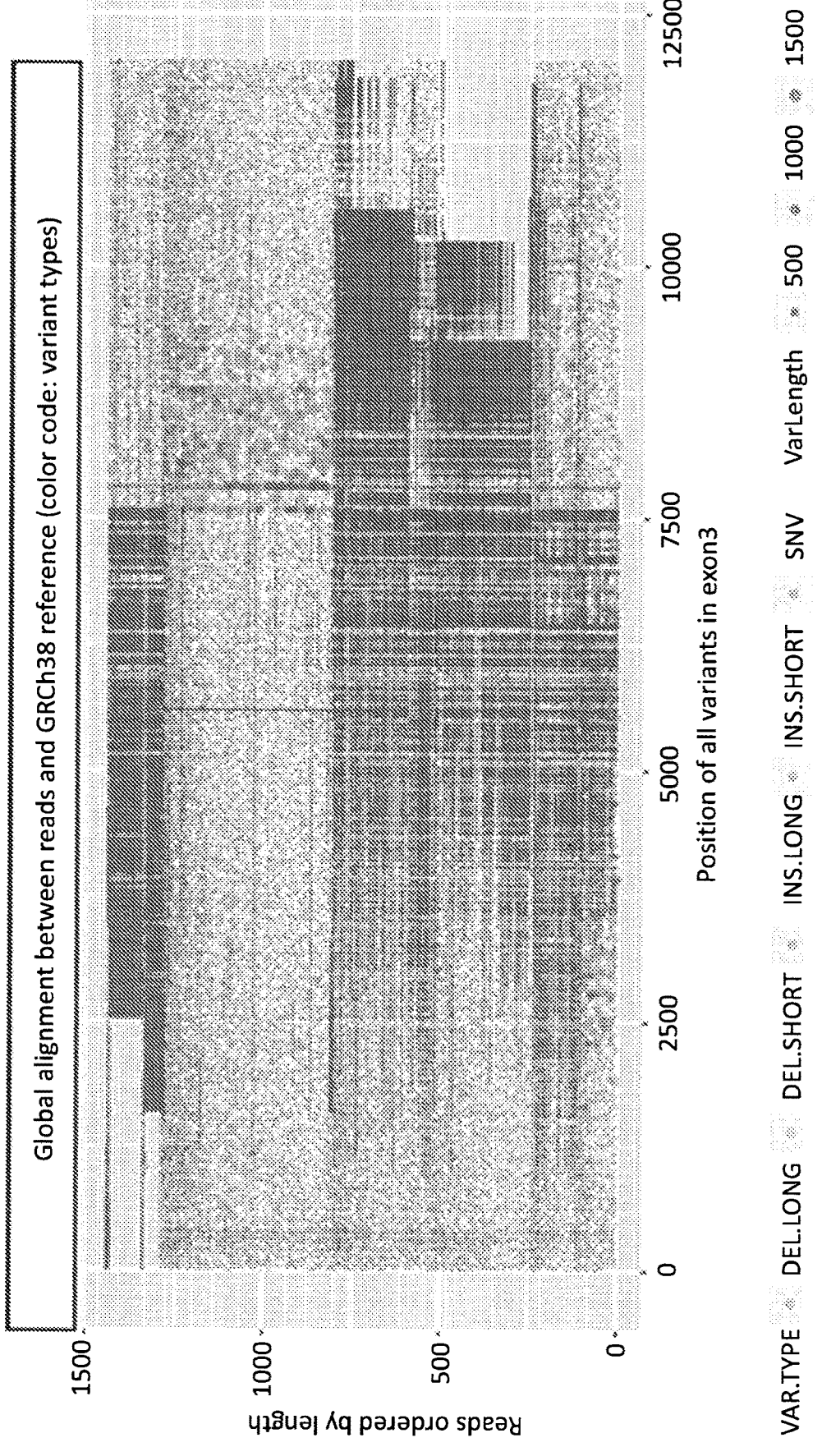
FIG. 12 shows global alignment between the read lengths generated and the Genome Reference Consortium Human Build 38 ("GRCh38") reference for exon 3, in accordance with an embodiment of the present disclosure.

FIG. 12 depicts unexpected noise in PacBio sequencing data. The figure displays a global alignment between the read lengths generated and the Genome Reference Consortium Human Build 38 ("GRCh38") reference for exon 3, according to an embodiment. Several variants are observed and a clear pattern of misalignment is present as indicated by the gaps visible in the alignment data at the right and left of the reads. These gaps are indicative of sequence generated insertions or deletions that are artifacts of sequencing, and thus, reads including these must be excluded as sequence artifacts, or noise.

Figures 13A, 13B:
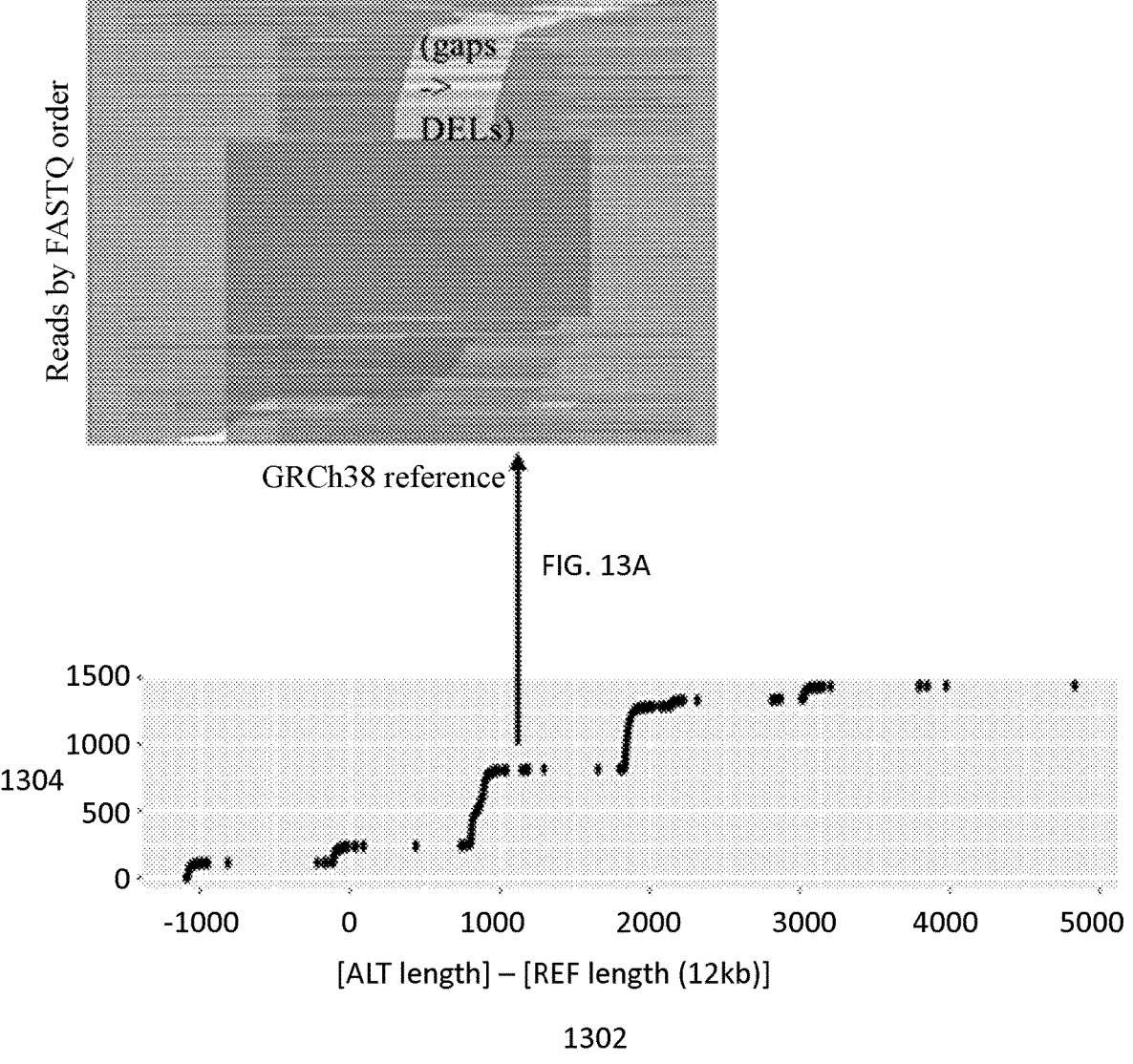
FIG. 13A depicts the order of alignment among a set of reads.
FIG. 13B depicts the size of these reads, in reference to their size against the actual read length.

FIGS. 13A and 13B depict the alignment of a set of random reads from one individual against GRCh38 FLG using MUMmer 3.23, according to an embodiment. FIG. 13A depicts the order of alignment among a set of reads. Several different read length groups were observed due insertions or deletions which occurred during the sequencing of the 13 kb length read. FIG. 13B depicts the size of these reads, in reference to their size against the actual read length. The x-axis 1302 indicates the difference in length of the read against the reference. The y-axis 1304 indicates the number of reads of that size.

Figure 14A:
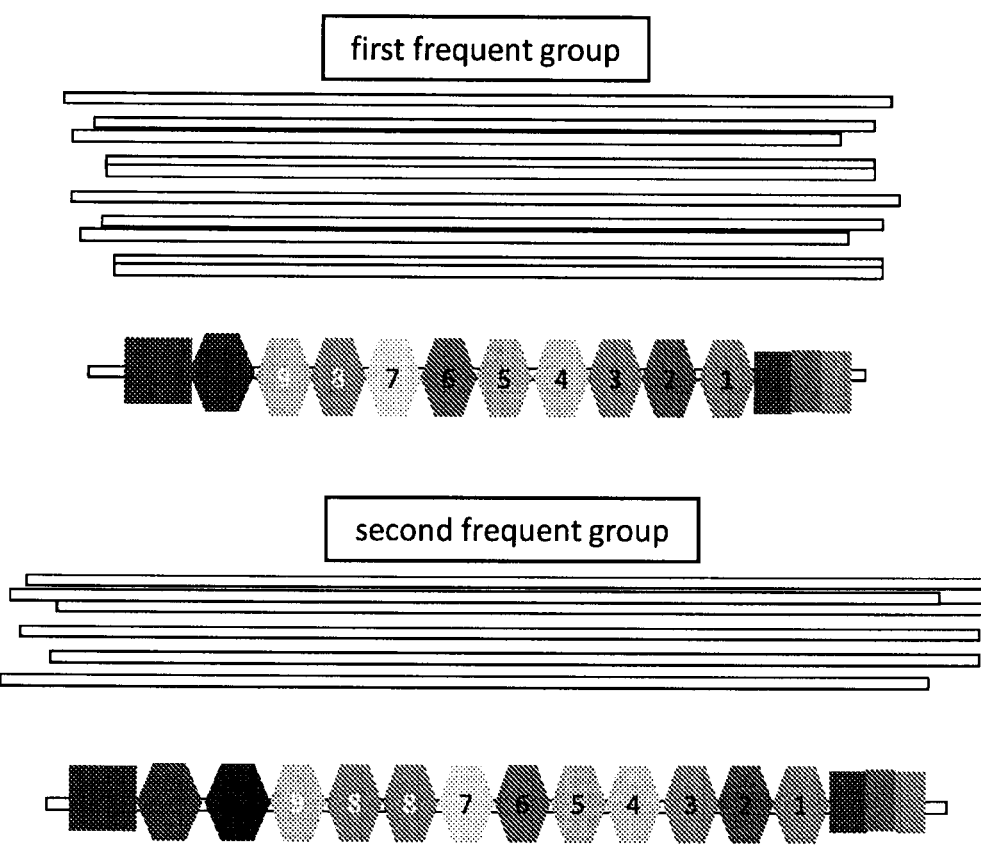
FIG. 14A is a schematic diagram of structures of an individual sample's first and second frequent groups, in accordance with an embodiment of the present disclosure.
Figure 14B:
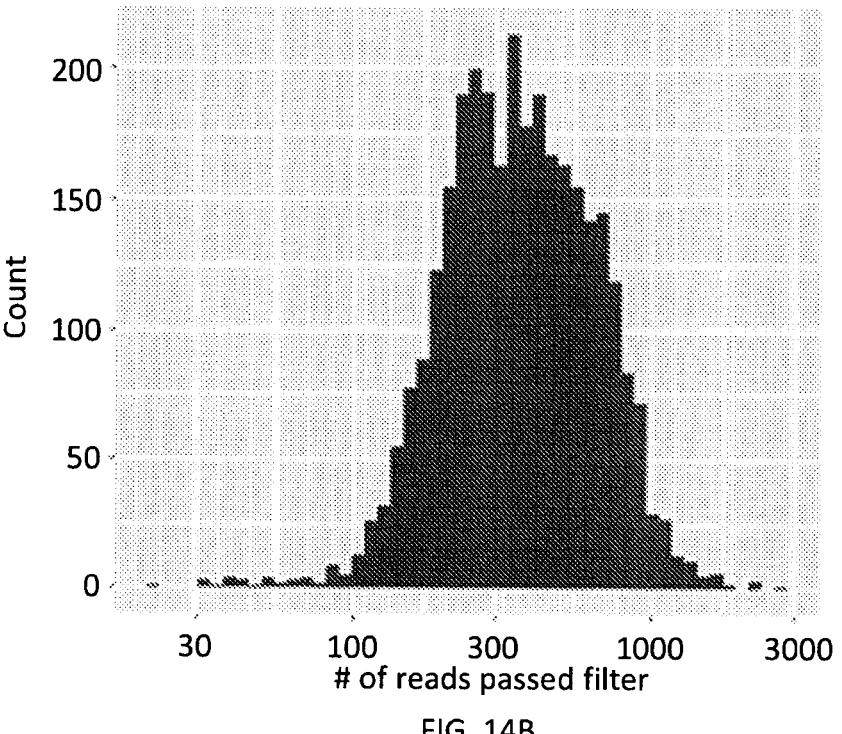
FIG. 14B is a histogram showing the distribution of passed-QC reads of ~3,000 individuals, after filtering the 3rd and later frequent groups, in accordance with an embodiment of the present disclosure.

FIGS. 14A and 14B depict the filtering of sequencing noise based on the structure. FIG. 14A depicts structures of a CN-HET individual sample's first and second frequent groups, according to an embodiment. The reads are grouped together based on a common structure, which is shown in the box and hexagon shapes. FIG. 14B depicts the graphing of the reads to show the number of the reads within each group based on the read group frequencies from smallest to largest.

Figure 15:
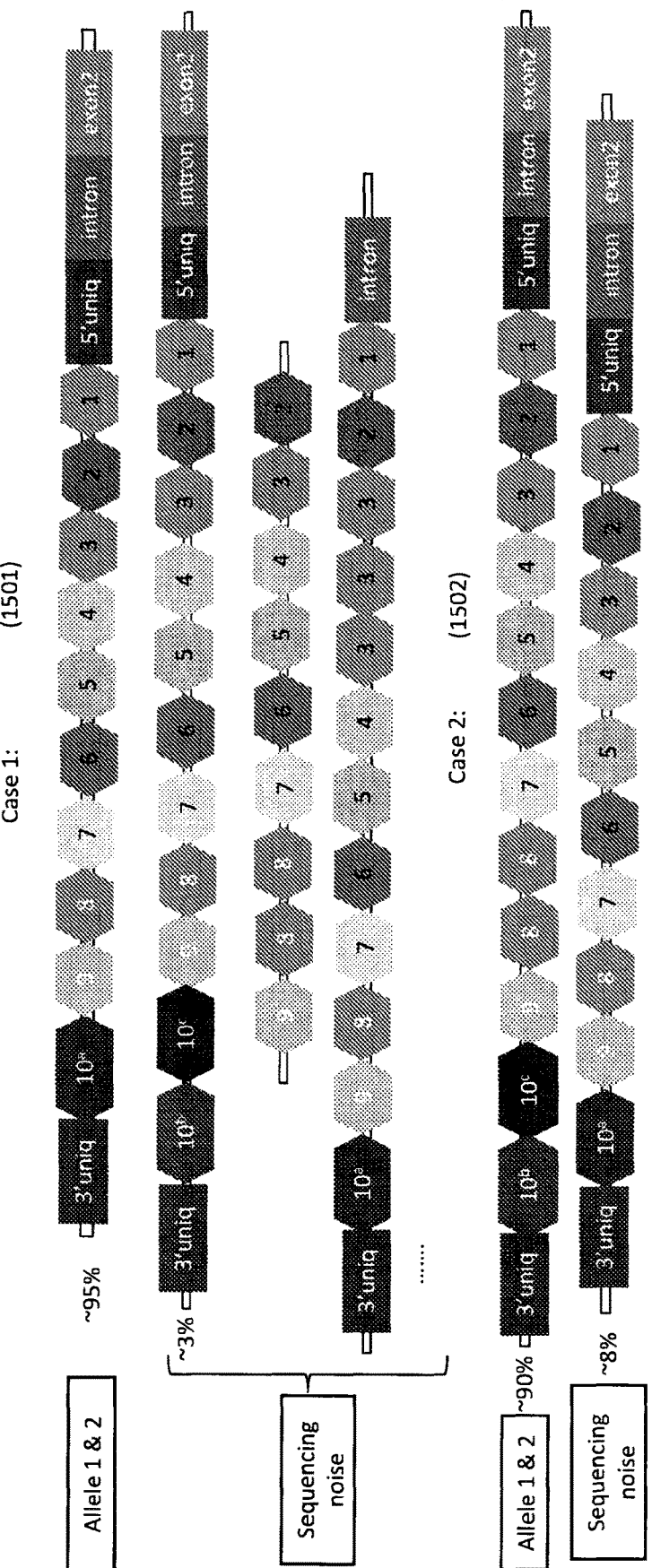
FIG. 15 is a schematic diagram depicting two example scenarios of the analysis of the imbalance rate and allele lengths of the most frequent read groups, where the individual is determined to be CN-HOM, in accordance with an embodiment of the present disclosure.

FIG. 15 depicts an analysis for detecting CN-HOM samples by investigating imbalance rate and allele length, according to an embodiment. FIG. 15 depicts two example scenarios of the analysis of the imbalance rate and allele lengths of the most frequent read groups, where the individual is determined to be CN-HOM. Case 1 (1501) depicts a scenario where 95% of the individual's sequencing reads are of a first frequent group, and there is no clear second frequent group. Because there is no clear second frequent group, the individual is determined to be CN-HOM. Case 2 (1502) depicts a scenario where approximately 90% of the individual's sequencing reads are of the first frequent group, and approximately 8% are of the second frequent group. Because the second frequent group contains a CN less than that of the first frequent group, the individual is determined to be CN-HOM.

Figure 16:
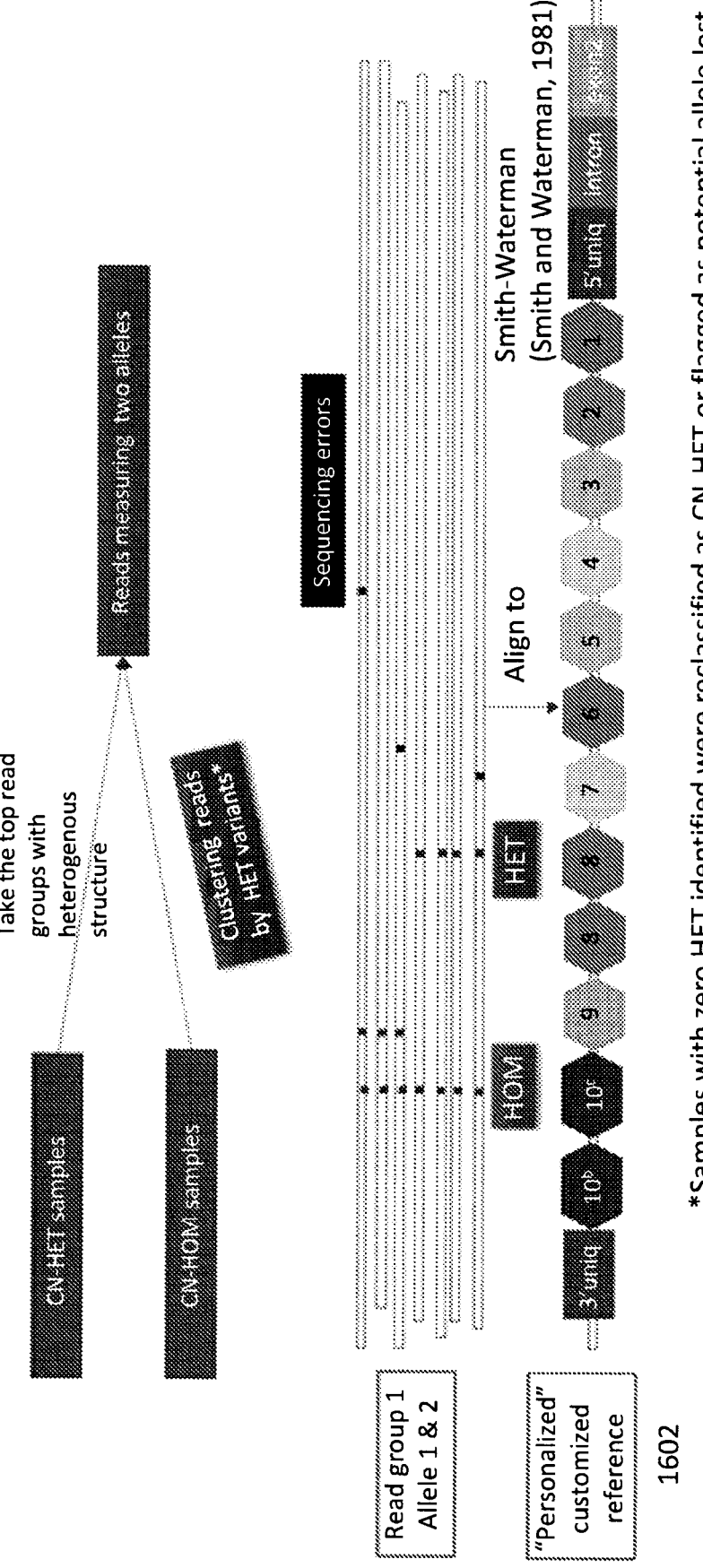
FIG. 16 is a schematic diagram showing two separate alleles identified in one read group identifying a heterozygous genotype, in accordance with an embodiment of the present disclosure.

FIG. 16 depicts the identification of a CN-HOM individual's alleles via an analysis against a customized reference, according to an embodiment. After sequence alignment against a personalized custom reference 1602, the alleles are separated via an analysis heterozygous SNP. The reads are then separated by their corresponding allele, according to their alignment. Two larger alleles are identified over a smaller allele.

FIG. 17 depicts three different variants 1702, 1704, 1706 with the overall PTV/pLoF burden 1708 observed within the current study, according to an embodiment. More particularly, FIG. 17 compares the identified potential loss of function mutations against those previously analyzed in the same gene. The frequency ratio of the variants were approximately three-fold higher within the patient populations as compared to the general population. A stop gain is a mutation by where a premature stop codon is gained leading to premature cessation of translation. Two stop gain mutations were observed: 1) At position 501 (e.g., variant 1702) the Arginine is now a termination codon and 2) at position 2447 (e.g., variant 1706) the Arginine is now a termination codon. A frameshift is an insertion or deletion of nucleotide bases, not in multiples of three. One frameshift mutation was observed at position 761 (e.g., variant 1704) by where a Serine is translated to a Cysteine. pLoF burden 1708 is predicted loss of function.

Figure 18:
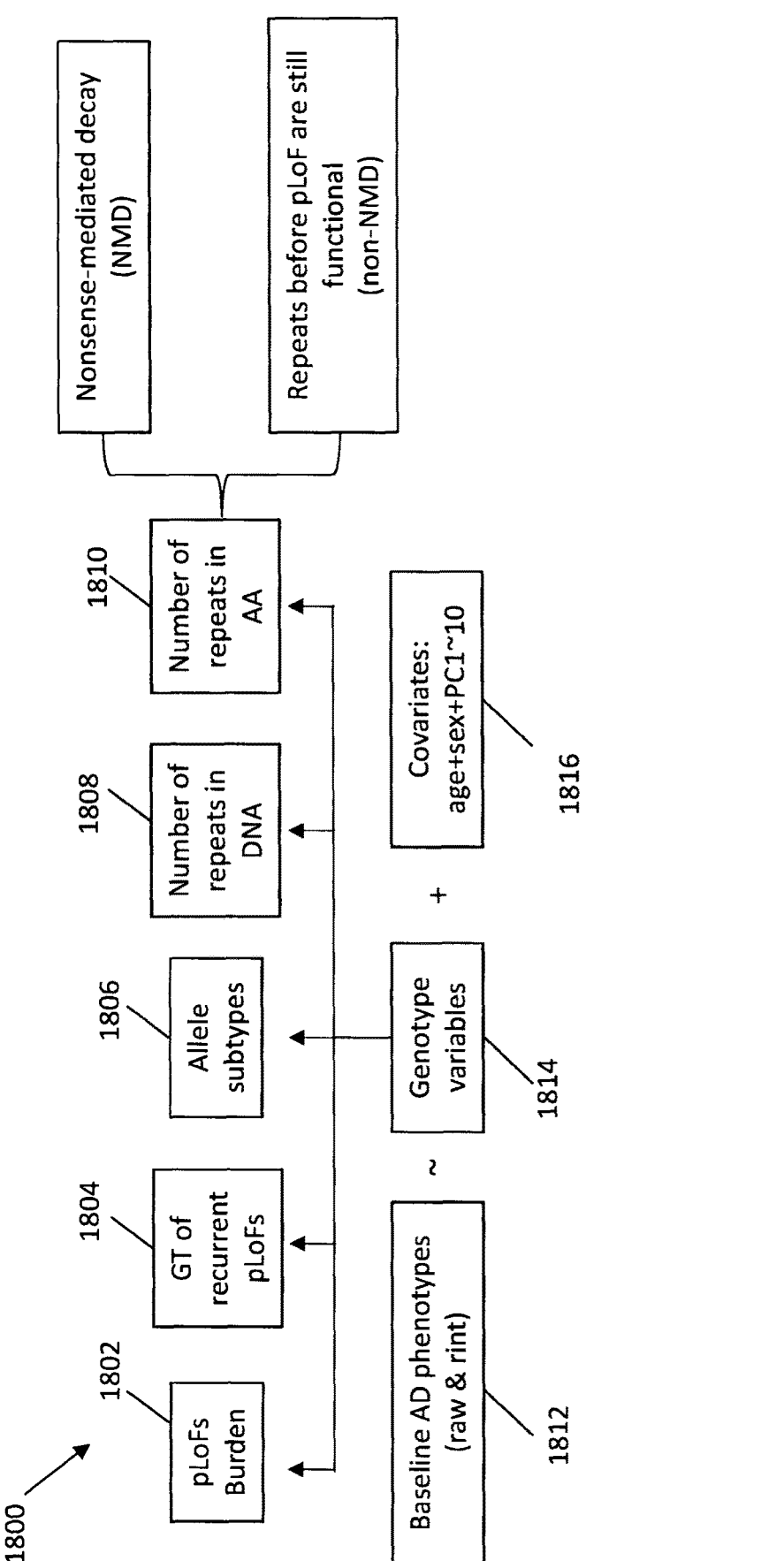
FIG. 18 is a schematic diagram showing the association tests performed between variables describing FLG genotypes and baseline disease phenotypes of atopic dermatitis (AD), in accordance with an embodiment of the present disclosure.

FIG. 18 depicts the results summary for tested genotype variables for Filaggrin and Atopic Dermatitis ("AD"), according to an embodiment. To test the hypothesis that FLG genotype—measured by pLoF burden 1802, dosage of recurrent pLoF variants 1804, structural allele 1806, copy number of functional repeats in DNA 1808, and/or copy number of functional repeats in the amino acid sequence 1810—was associated with baseline AD disease severity 1812. Further, multiple linear regression tests were run between the genotype variables 1814 and phenotype variables 1812, with age, sex, and first 10 genetic PCs as covariates 1816.

Figure 19A:
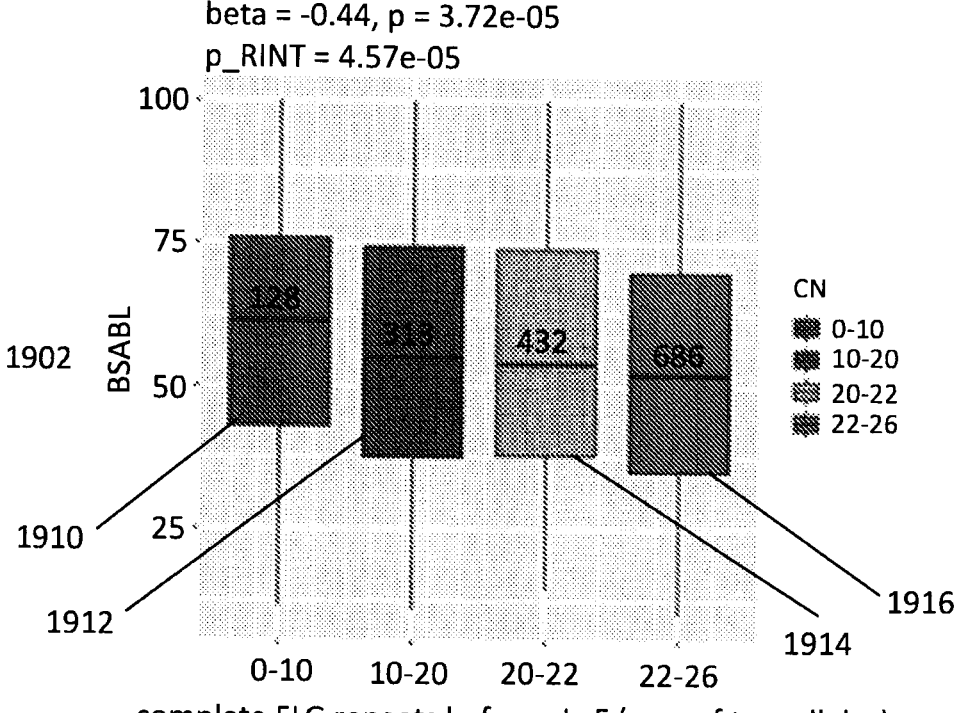
FIG. 19A is a boxplot showing a body surface area baseline clinical phenotype in association with the copy number of functional repeats, in accordance with an embodiment of the present disclosure.
Figure 19B:
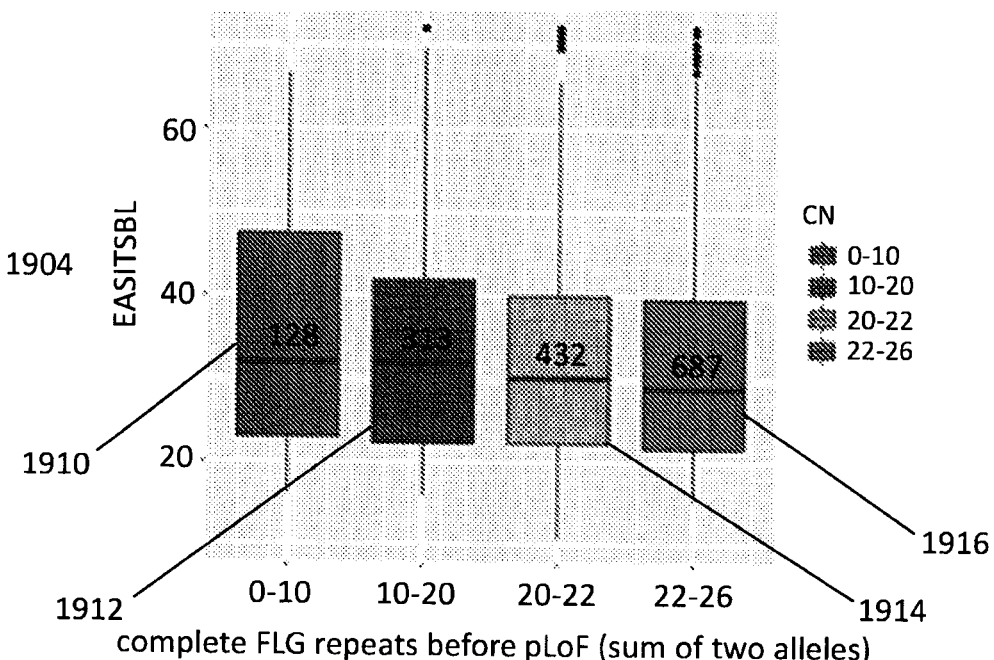
FIG. 19B is a boxplot showing an Eczema Area and Severity Index baseline clinical phenotype in association with the copy number of functional repeats, in accordance with an embodiment of the present disclosure.
Figure 19C:
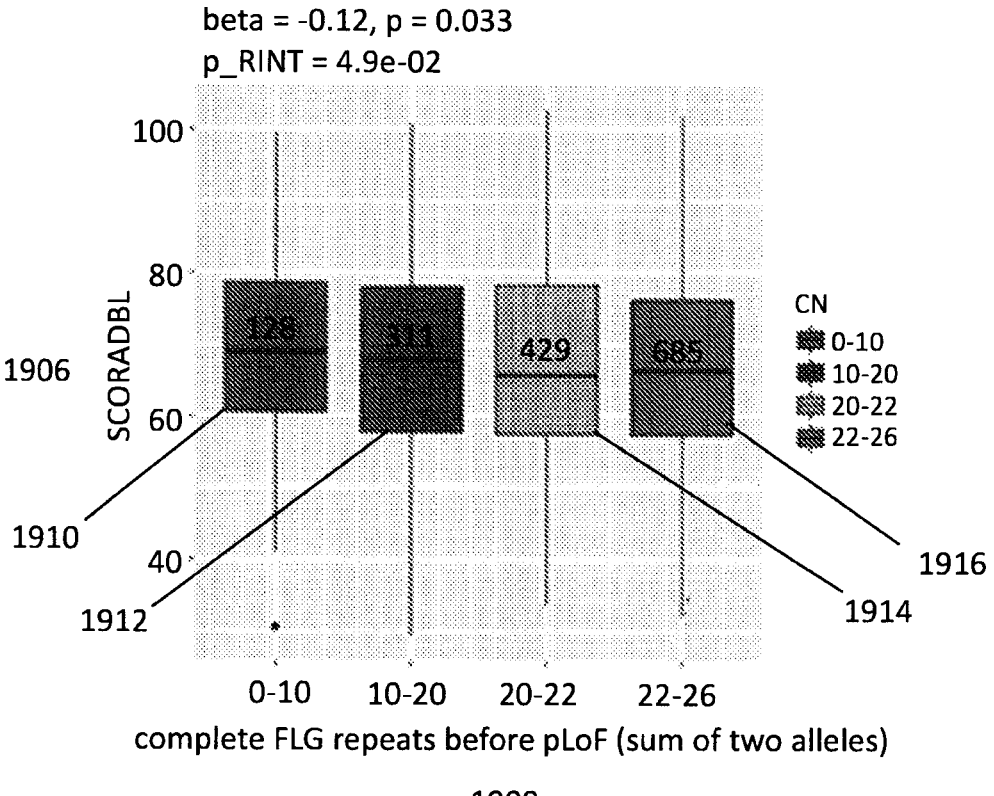
FIG. 19C is a boxplot showing a SCORing Atopic Dermatitis Score baseline clinical phenotype in association with the copy number of functional repeats, in accordance with an embodiment of the present disclosure.

FIGS. 19A-19C are boxplots depicting baseline clinical phenotypes in association with the copy number of functional repeats (counting repeats completely translated to amino acid sequences, and sum the counts from both alleles) 1908, according to an embodiment. More particularly, BSABL 1902 in FIG. 19A is body surface area baseline, EASITSBSL 1904 in FIG. 19B is Eczema Area and Severity Index baseline, and SCORADBL 1906 in FIG. 19C is SCORing Atopic Dermatitis Score baseline. The copy number variables ranged from 0-10 (1910), 10-20 (1912), 20-22 (1914) and 22-26 (1916). The association observed here provides evidence that the genotyping calling algorithm is accurate and working. Patients with lower functional copy numbers have more severe disease, as would be expected.

Figure 20:
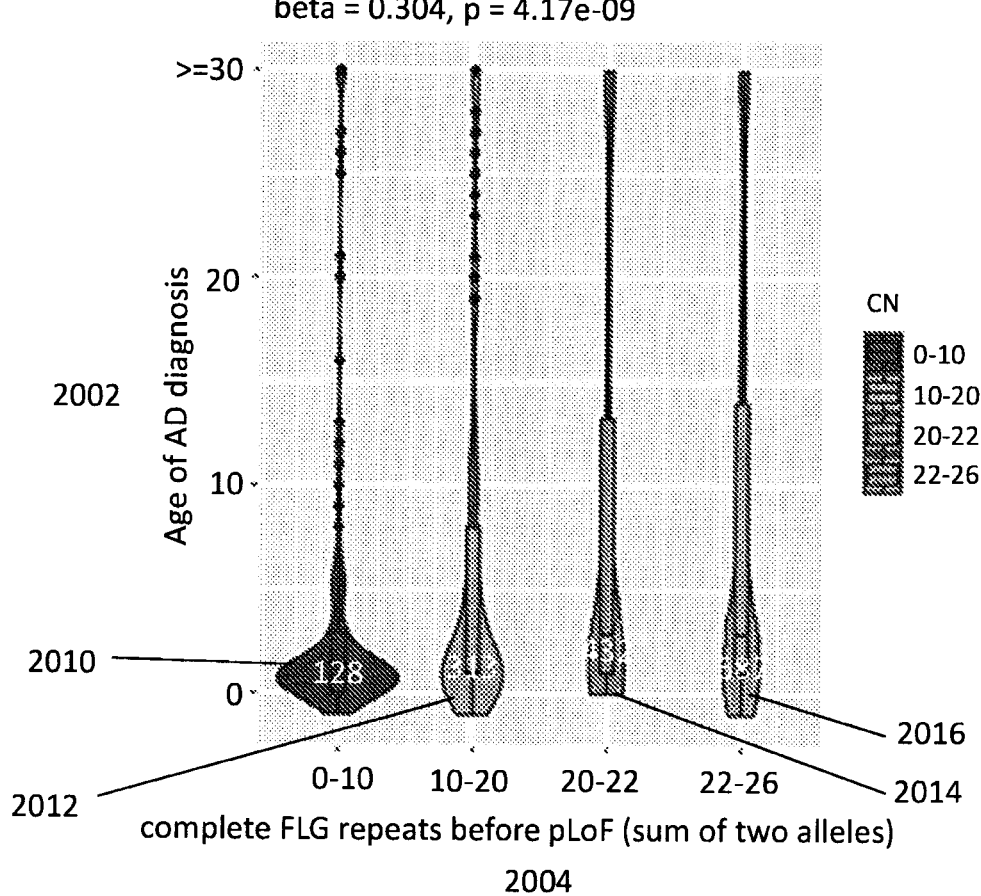
FIG. 20 is a graph showing the relationship of age of diagnosis of Atopic Dermatitis ("AD") with copy number, in accordance with an embodiment of the present disclosure.

FIG. 20 is a graph depicting the relationship of age of diagnosis of AD 2002 with copy number 2004, according to an embodiment. The copy number variables ranged from 0-10 (2010), 10-20 (2012), 20-22 (2014) and 22-26 (2016) and the age range was from 0 to over 30. The association observed here provides evidence that the genotyping calling algorithm is accurate and working. Patients with lower functional copy numbers develop AD at an earlier age.

Figure 21A:
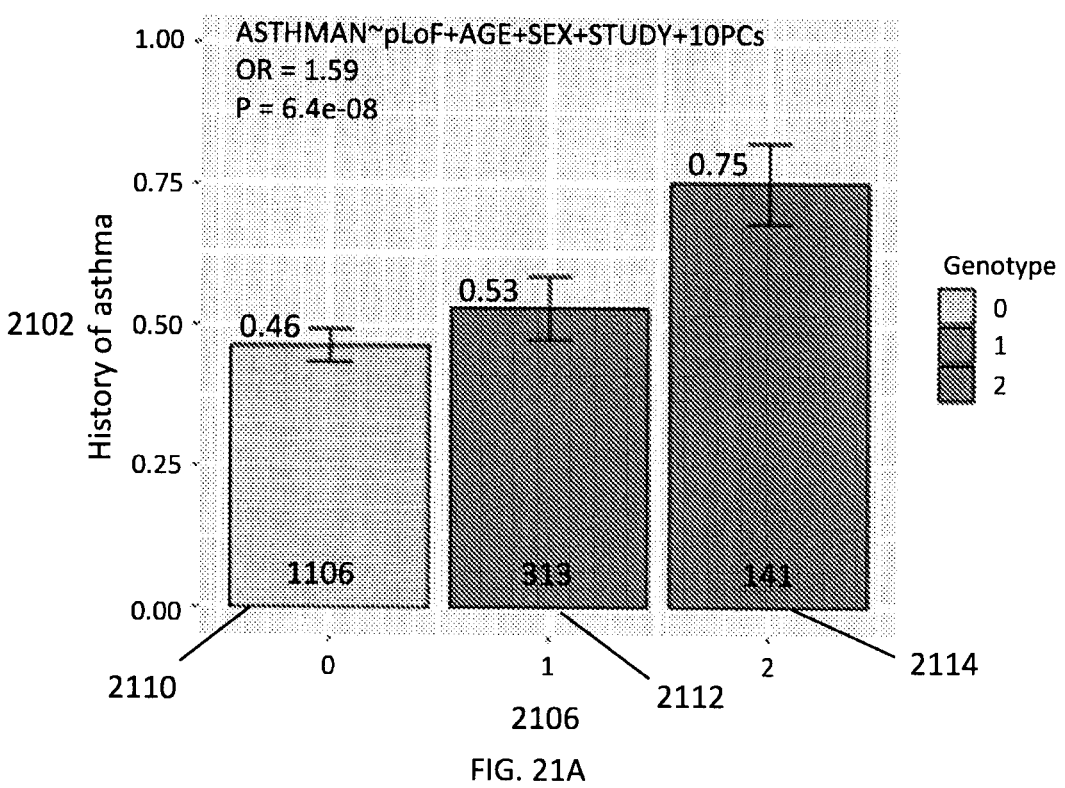
FIG. 21A is a graph showing the relationship of number of alleles carrying FLG PTVs associated with a history of asthma in patients with AD.
Figure 21B:
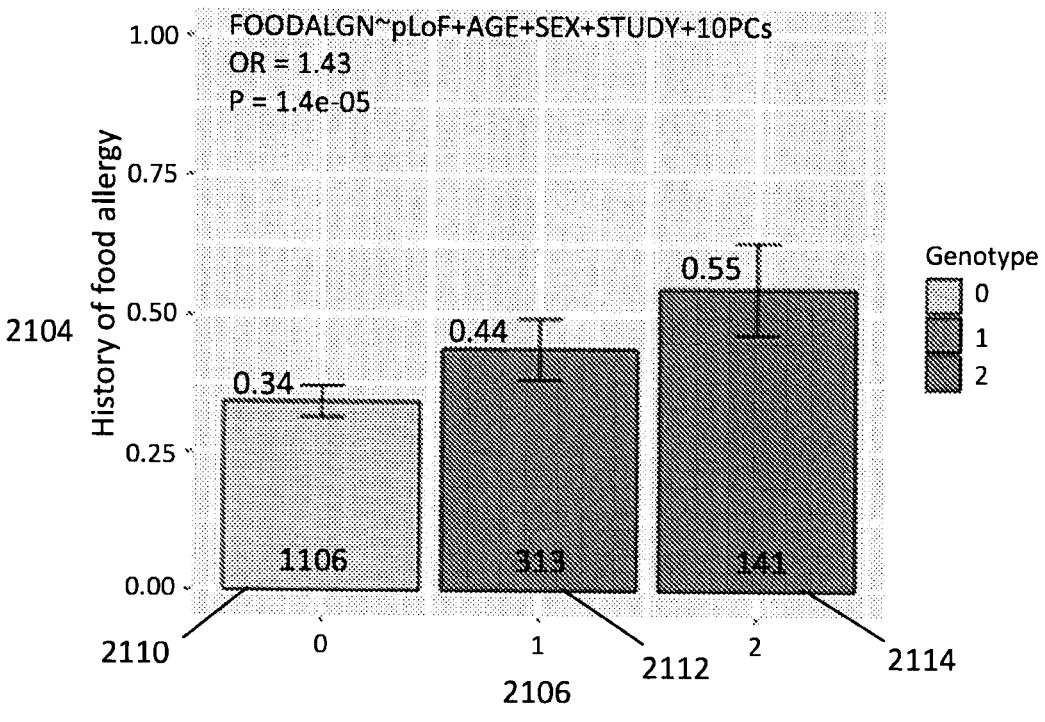
FIG. 21B is a graph showing the relationship of number of alleles carrying FLG PTVs associated with a history of food allergy in patients with AD, in accordance with an embodiment of the present disclosure.

FIGS. 21A and 21B are graphs depicting the relationship of FLG genotypes 2106 with pLoF associated with a history of asthma 2102 or a history of food allergy 2104 in patients with AD, according to an embodiment. The association observed here provides evidence that the genotyping calling algorithm is accurate and working. Patients with lower functional copy numbers have an increased risk of developing asthma and food allergies. Both are known comorbidities with AD. Genotype number, as depicted in FIGS. 21A and 21B, corresponds with the occurrence of PTVs in the individual samples' alleles. An individual was categorized as Genotype 0 (2110) if neither of their alleles contained PTVs, Genotype 1 (2112) if one allele contained a PTV, and Genotype 2 (2114) if both their alleles contained PTVs.

Figure 22A:
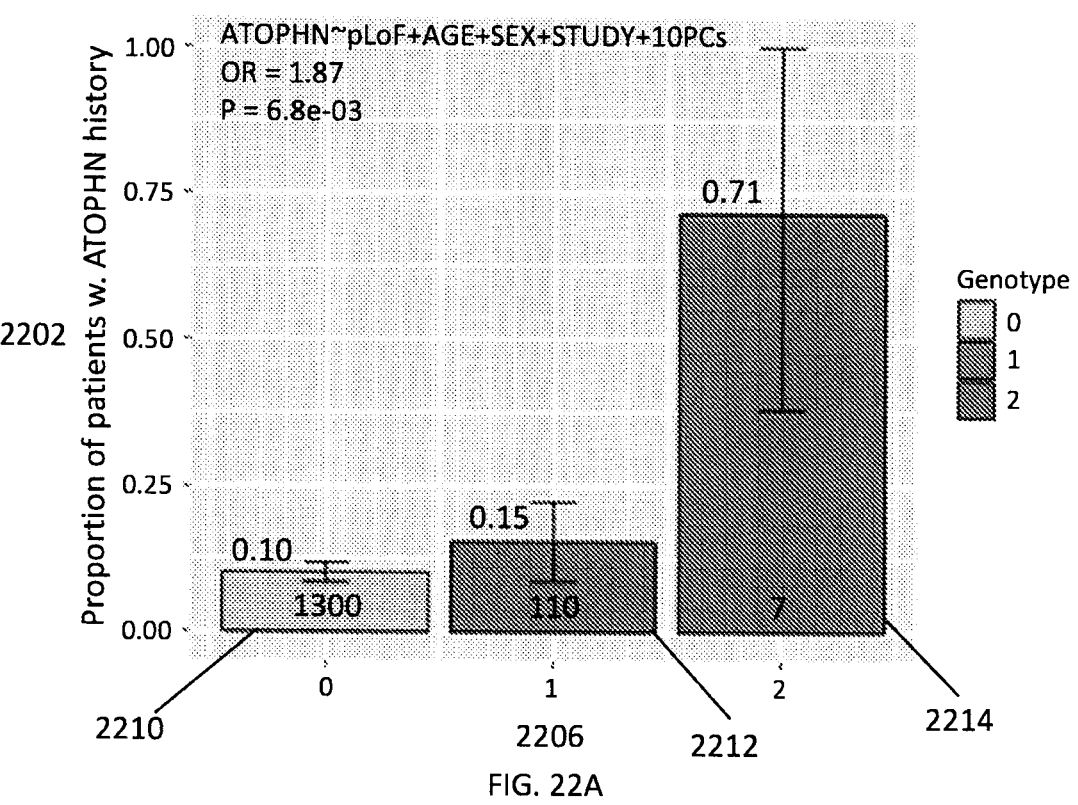
FIG. 22A shows the relationship of number of alleles carrying FLG PTVs with a history of AD in patients with asthma.
Figure 22B:
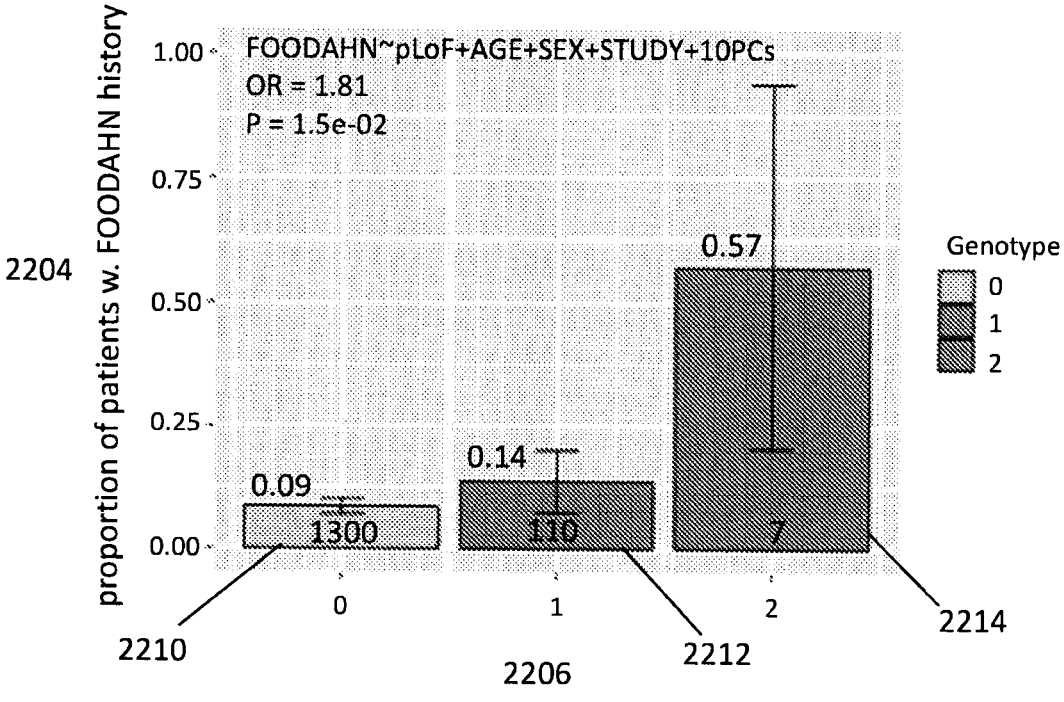
FIG. 22B shows the relationship of number alleles carrying FLG PTVs with a history of food allergy, in accordance with an embodiment of the present disclosure.

FIGS. 22A and 22B are graphs depicting the relationship of FLG genotypes 2206 with pLoF associated with a history of AD 2202 or a history of food allergy 2204 in patients with Asthma, according to an embodiment. The association observed here provides evidence that the genotyping calling algorithm is accurate and working. Asthma patients with lower functional copy numbers have an increased risk of developing AD and food allergies. Genotype number, as depicted in FIGS. 22A and 22B, correspond with the occurrence of PTVs in the individual samples' alleles. An individual was categorized as Genotype 0 (2210) if neither of their alleles contained PTVs, Genotype 1 (2212) if one allele contained a PTV, and Genotype 2 (2214) if both their alleles contained PTVs.

Figure 23:
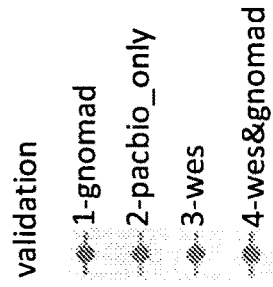
FIG. 23 is a graph illustrating the known and novel validated PacBio PTVs from exon 3, in accordance with an embodiment of the present disclosure.

FIG. 23 depicts the known and novel PTVs mapped via frameshift, pLoF and stop gain corresponding to their position on exon 3, according to an embodiment. The known PTVs were validated through internal WES data measuring, as well as gnomAD. The dataset was evaluated by HWE and no structural alleles were excluded. PTVs, however, were not evaluated through HWE as they are present in low frequency. The novel PTVs have never been described previously.

Figure 24:
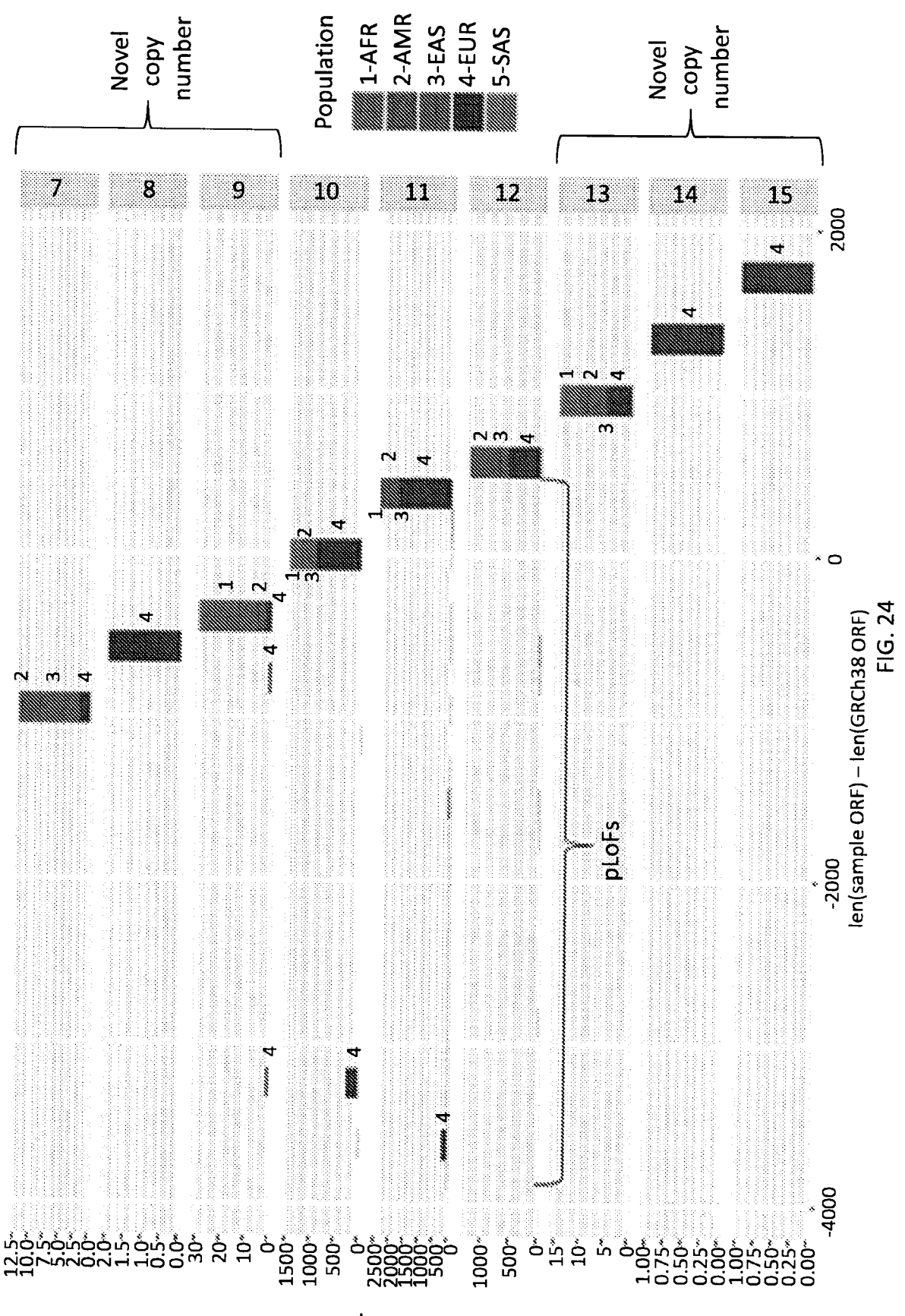
FIG. 24 is a graph illustrating anticipated and novel copy number, in accordance with an embodiment of the present disclosure.

FIG. 24 depicts the identification of known and novel copy number alleles validated through correlation of the ORFs with DNA copy number, according to an embodiment. Novel structural alleles that have not been previously described, were identified both smaller and larger than the anticipated copy number. The novel structural alleles were enriched in samples of African, European or East Asian ancestry.

Figure 25:
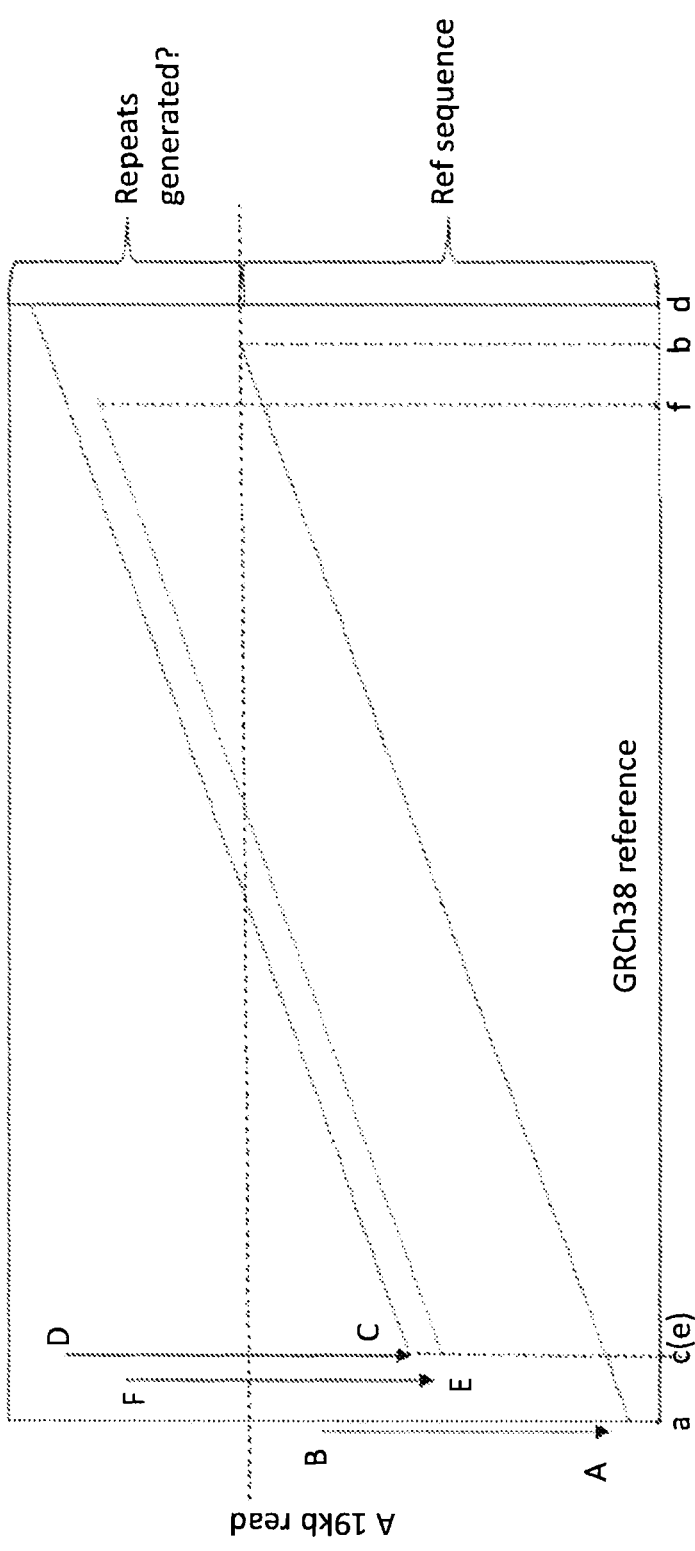
FIG. 25 is a graph showing an example of the artifact introducing amplification of repeats during PacBio sequencing, which was visualized by aligning the abnormally long (19 kb) read to the reference FLG sequence (GRCh38), in accordance with an embodiment of the present disclosure.

FIG. 25 is a graph showing an example of a structural artifact introducing amplification of repeats during PacBio sequencing, which was visualized by aligning the abnormally long (19 kb) read to the reference FLG sequence (GRCh38), in accordance with an embodiment of the present disclosure.

Figure 26:
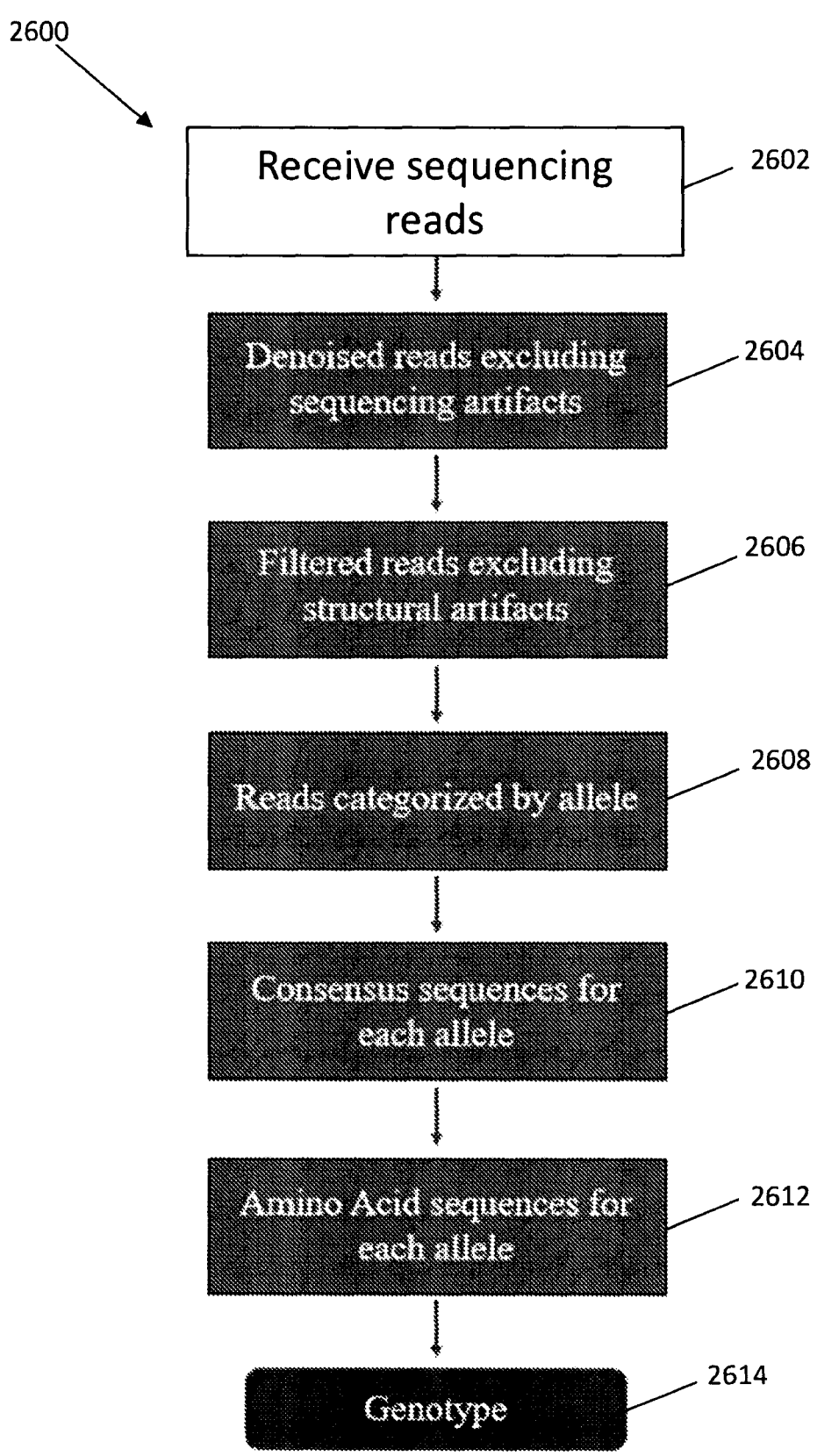
FIG. 26 is a flow diagram of a process for transforming an input dataset into the genotype of the individual sample, in accordance with an embodiment of the present disclosure.

FIG. 26 is a flow diagram of a process for transforming an input dataset into the genotype of the individual sample 2600, in accordance with an embodiment of the present disclosure. At 2602, an input set of sequencing data is received. Next, at 2604, the input set of sequencing data is denoised to generate a first dataset, the first dataset excluding reads with sequence artifacts. The reads of the first dataset are then filtered to generate a second dataset, the second dataset excluding sequences with structural artifacts at 2606. Next, at 2608, the reads in the second dataset are categorized by allele to generate a third dataset. In some embodiments, the reads may be classified into reads for each allele via an AI/ML model. In further embodiments, the AI/ML model includes a single-step classifier and/or a multi-step classifier. For example, in some embodiments, the AI/ML model includes a k-means clustering algorithm. A consensus sequence for each allele in the third dataset is generated to generate a fourth dataset at 2610. Each allele of the fourth dataset is translated to generate a fifth dataset, the fifth dataset including the correspondence amino-acid sequence of each allele at 2612. Then, at 2614, the genotype of the individual is determined based on the amino-acid sequences of the fifth dataset.

EXAMPLES

Example 1

Patient Population
The analyses comprised data from seven clinical trials in dupilumab: two asthma studies and five studies in atopic dermatitis.
Asthma
The DRI12544 study was a randomized, double-blind, placebo-controlled, parallel-group, pivotal phase 2b clinical trial. The study enrolled individuals with asthma aged ≥18 years. Patients were randomly assigned (1:1:1:1:1) to receive subcutaneous dupilumab 200 mg or 300 mg every 2 weeks or every 4 weeks, or placebo.

The EFC13579 study was a phase 3, double-blind, placebo-controlled, parallel-group trial (NCT02414854) in patients with persistent asthma. Patients 12 years and older were randomized in a 2:2:1:1 ratio to receive add-on therapy of dupilumab 200 or 300 mg every 2 weeks or placebo.

The primary efficacy endpoints in both asthma studies were absolute change from baseline in pre-bronchodilator FEV1 at week 12 and annualized rate of severe exacerbation events.
Atopic Dermatitis
Phase 2 Studies:
Study 1307 was a placebo-controlled, double-blind, phase 2 trial. Patients 18 years or older were randomized 1:1 to weekly 200 mg of dupilumab or placebo. Study 1021 was a phase 2b placebo-controlled, double-blind study in patients ≥18 years. Patients were randomly assigned (1:1:1:1:1:1) to dupilumab 300 mg once a week, 300 mg every 2 weeks, 200 mg every 2 weeks, 300 mg every 4 weeks, 100 mg every 4 weeks, or placebo once a week. The primary end point for both phase 2 studies was mean percentage change from baseline to week 16 in EASI score.
Phase 3 Studies:
Studies 1334 and 1416 were placebo-controlled, phase 3 trials of identical design (SOLO 1 and SOLO 2), which enrolled individuals ≥18 with moderate-to-severe atopic dermatitis whose disease was inadequately controlled by topical treatment. Patients were randomly assigned in a 1:1:1 ratio to dupilumab (300 mg) or placebo weekly or the same dose of dupilumab every other week alternating with placebo. The primary outcome was the proportion of patients who had both a score of 0 or 1 (clear or almost clear) on the Investigator's Global Assessment and a reduction of 2 points or more in that score from baseline at week 16.

Study 1224 was a placebo-controlled, phase 3 trials for adults ≥18 years old with moderate-to-severe atopic dermatitis and inadequate response to topical corticosteroids. Patients were allocated (3:1:3) to dupilumab 300 mg once weekly (qw), dupilumab 300 mg every 2 weeks (q2w), or placebo. All study arms were given concomitant topical corticosteroids. The IGA primary endpoints were identically defined as the other Atopic Dermatitis studies, an additional co-primary endpoint was EASI-75 (Eczema Area and Severity Index 75% improvement) from baseline at week 16.

Example 2

DNA samples were processed and the 13.5 kb region encompassing filaggrin exon 2 and 3 was amplified using a 2-step PCR process to generate 96 barcoded amplicons for multiplexed sequencing on the PacBio Sequel II system. Target-specific sequences tailed with universal adapter sequences were used to amplify the filaggrin locus. In the second round of PCR, each amplicon was barcoded using primers with the universal sequence tailed with a unique barcode sequence. The barcoded amplicons were analyzed for the presence of 1 kb increment banding in a region ranging in size from 1-18 kb by automated electrophoresis on an Agilent ZAG DNA Analyzer System. Agilent ProSize software was used to run a smear analysis from 9-18 kb to quantify the molarity of the desirable portion of each amplicon (9-18 kb) from the undesirable portion (1-9 kb).

Samples were sequenced in ninety-six sample increments and pooled equimolarly based on a 9-18 kb smear analysis. To remove the extraneous 1-9 kb portion, the multiplexed amplicon pool was run through the SageELF electrophoresis system to separate the DNA by size and fractionate the whole sample into 12 fractions ranging in size from 1-18 kb. The estimated width of each fraction is determined by the SageELF instrument. The size of the 12 fractions was determined by automated electrophoresis on an Agilent ZAG DNA Analyzer System. Three fractions with a size greater than 9 kb were pooled together and used to prepare a PacBio SMRTbell library for sequencing on the PacBio Sequel II according to the manufacturer's recommendations. Sequencing data was generated by the CCS software as part of the Pacbio SMRT® Link package.

Example 3

FLG Genotyping Pipeline
3.1 Identify the Technical Artifacts in the Sequencing Data
Based on the four types of the structural alleles that were previously known, it was expected that the lengths of the PacBio reads would be approximately 13 kb, 14 kb, or 15 kb. For each individual, there should be either one type of read length (from two alleles with the same number of repeats, represented as "CN-HOM") or two types of read lengths (from two copy-number-different alleles, represented as "CN-HET"), the ratio of which should be close to 1:1. However, for most individuals, the read length distribution had a wide range of possible values, some of which were longer than 15 kb or shorter than 13 kb.

Another approach was attempted by clustering reads by the length around 13 kb, 14 kb, and 15 kb. It was observed that the size ratio was rarely equivalent between any two read groups. The possible technical artifacts involved were as follows: 1) PCR bias: for CN-HET individuals, PCR over amplified the shorter FLG allele over the longer allele, causing an imbalance in sequencing depth across the alleles; 2) Sequencing-introduced insertion/deletion: due to the repetitive structure of exon 3 and the mechanism of long-reads sequencing technology, extra insertions/deletions were introduced into some of the reads. The visualization of this artifact can be found in FIG. 11, in which a set of random reads from each read-length group of one individual were aligned against GRCh38 FLG reference using MUMmer 3.23.
3.2 Measure Repeat Structure to Filter Sequencing Noise
When investigating the sequence structure of the repeats, the first 9 repeats and the three forms of repeat 10 were highly similar, yet different enough from each other to be uniquely aligned to the reference using local aligner with default parameters. The structural information provided by the local alignment was used to filter out the sequencing noise. The reference sequence was split into regions representing exon 2, intron, exon 3 unique region near the 5' end, repeats 1-9, 10a, 10b and 10c, and exon 3 unique region near the 3' end, and aligned the 16 reference fragments to all the PacBio reads using minimap2 all-by-all alignment utility. Each read was then sorted by the alignment results by the starting position, and read out the order of reference fragments that aligned to it. For each individual, the structure of all the reads was summarized by BEDTools software and grouped reads with same sequence structure. The read groups were then ordered by frequencies (number of the reads within the group), from the largest to the smallest. Under the hypothesis that sequencing noises were random and sparse, the reads in the most frequent group of reads (the "first frequent group") and the second most frequent group of reads (the "second frequent group") were retained, assuming the rest contained artifact-introduced sequence variants.

3.3 Classify Reads by Allele
The next step of the pipeline was to classify the informative reads by the allele they represented, similarly to the concept of "phasing".

As mentioned in Example 3.1, samples having alleles with the same copy number are CN-HOM and samples with a different copy number are CN-HET. For CN-HET, samples from the first frequent group measured one allele, and sample from the second frequent group measured a second allele. For CN-HOM samples, both alleles were represented in the first frequent group, while the second frequent group was likely to be sequencing noise. The CN-HOM and CN-HET samples are distinguished via ML and/or AI. For example, in some embodiments, the CN-HOM and CN-HET samples are distinguished via an AI/ML model. In further embodiments, the AI/ML model includes a single-step classifier and/or a multi-step classifier.

Given that shorter alleles were over-amplified, the expectation was that for CN-HET samples, the first frequent group would be shorter than the second frequent group, otherwise the second frequent group was most likely to be rare sequencing noise, which means samples with a longer allele in the first frequent group were likely to be CN-HOM samples. Thus, individuals that showed a first frequent group of greater length that the second frequent group were classified as CN-HOM samples.

For samples having alleles with the same copy number but different structures, the frequencies between first and second frequent groups were expected to be similar (with a ratio close to one). If instead it was observed that the first frequent group was much more abundant (ratio>>1), the second frequent group was flagged as noise and the samples were classified as CN-HOM.

For samples having the first frequent group representing a shorter allele, a null distribution (the "expectation") was derived for the level of PCR-bias given the length differences of two alleles. PCR-bias was measured by the copy number of second frequent group minus the copy number of first frequent group. For example, given the first frequent group was one copy number shorter than the second frequent group (CNsecond–CNfirst=1), the distribution of the frequency ratios (Freqfirst/Freqsecond) was plotted in log scale, and it was assumed that the outliers were CN-HOM samples, where the second group was too rare to be considered as a true signal, even conditioned on the imbalanced sampling from PCR-bias. The same procedure was repeated for the subset of samples with (CNsecond–CNfirst=2), in which the imbalance rate was much higher. A few samples with CNsecond–CNfirst>2 were classified to CN-HET, considering the small number of observations were not efficient to derive the null.

After having the CN-HOM samples identified, the reads within the first frequent group were phased into two separate alleles. Since there was no more information obtainable from the structural variants, the two sets of reads were clustered by the genotype of smaller variants—SNPs and Indels. To improve the accuracy of the alignment, a customized reference sequence for each sample was first derived to mimic the structure of the two alleles of an individual. Global alignment (smith-waterman algorithm) was then applied between the reads in first frequent group and the customized reference to detect heterozygous (HET) SNPs/Indels (defined as mismatches with VAF~[0.25,0.8]). As the last step, a k-means (k=2) clustering algorithm was run on the genotype matrix of the HET SNPs and Indels to classify the reads into two allelic groups.

3.4 Detect Protein-Truncating Variants

If sufficient sequencing depth of both alleles (only samples with a number of reads ≥10 for the second group were included), the SPOA software was run to generate two consensus sequences for each individual in the dataset, representing the DNA sequences of FLG gene. These consensus sequences could be aligned to customized references to identify all the nucleic acid changes. However, considering the repeats normally form multiple filaggrin monomers to support the skin function, the DNA sequences were translated into amino acid sequence and the focus was on the protein-truncating variants (PTVs), which are more likely to have phenotypic effects.

Each consensus sequence was translated into the longest open reading frame (ORF) using the getorf utility from EMBOSS package, requiring the starting sequence to be the same or similar to the reference. Next, the translated ORF is compared to the expected ORF length given the number of repeats on exon3, and called a PTV if the observed sequence is shorter. Next, the truncated ORF was aligned to the reference amino acid sequence to be classified as either a stop gain variant or frameshift variant. The position and the amino acid of the last aligned base are recorded to define the location of the specific PTV. The method was run on both alleles of all samples to annotated and capture the allele frequency of recurrent PTVs.

3.5 Callset Quality Evaluation

PTVs were validated by internal Whole Exome Sequencing ("WES") data measuring the same set of samples, as well as external database gnomAD (see Karczewski et al., 2020), a genetics dataset including the exome and genome sequencing data of 141,456 multi-ethnic individuals.

The quality of copy number genotypes for FLG repeats was evaluated by HWE tests. HWE was calculated in the each genetically determined ancestral subgroup (African, East Asian, Admixed American, European, South Asian) as deemed appropriate. No significant deviations from HWE ($p<1\times10^{-6}$) were observed in any of the ancestral populations. Thus, the method disclosed herein accurately determined the copy number genotypes for FLG repeats.

Further identification of known and novel copy number alleles was validated through correlation of the ORFs with DNA copy number. Novel structural alleles were identified both smaller and larger than the anticipated copy number. The novel structural alleles were enriched in samples of African, European or East Asian ethnicity. The known and novel PTVs were then mapped via frameshift, pLoF and stop gain corresponding to their position on exon 3. The known PTVs were validated through internal WES data measuring, as well as gnomAD.

Figure 27:
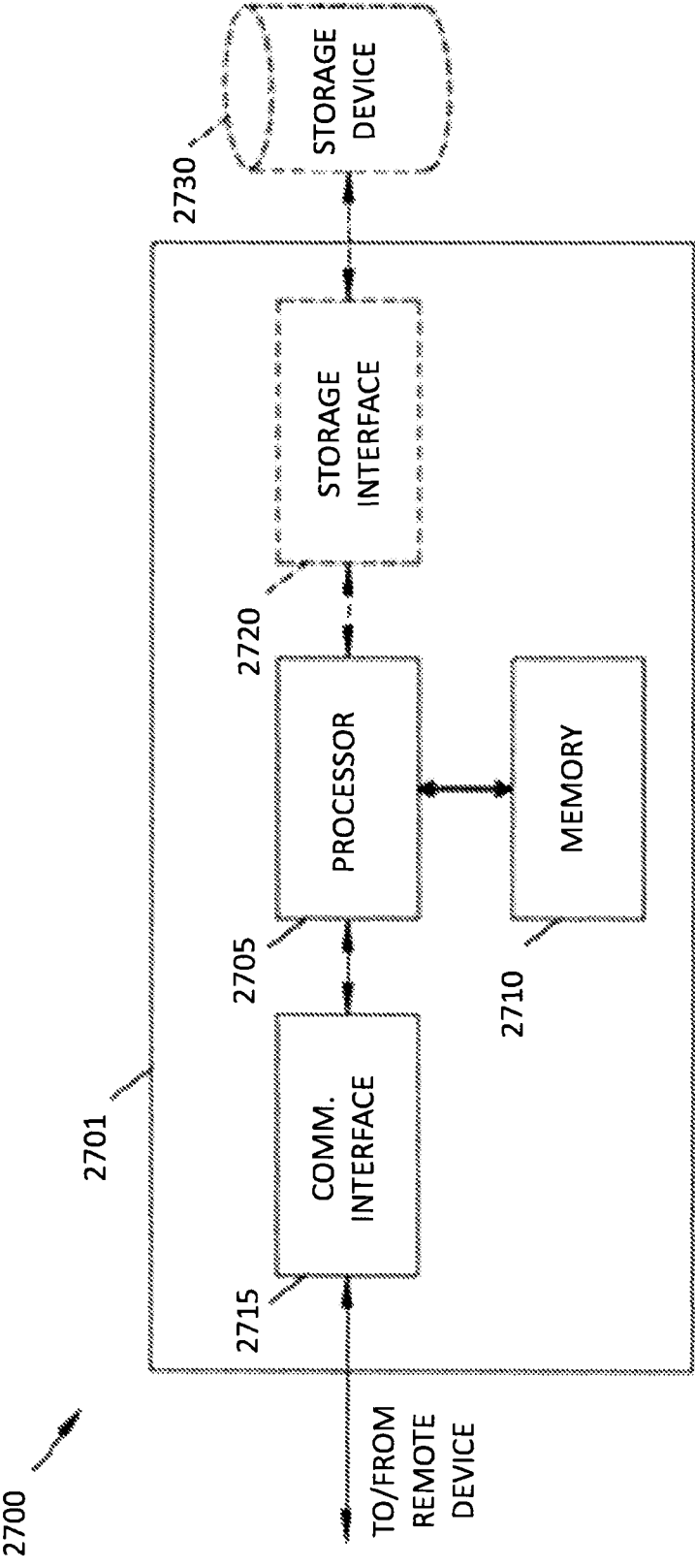
FIG. 27 is a block diagram of a server computing device that may be used with the computer system of FIG. 1, in accordance with an embodiment of the present disclosure.

Example server computing devices are disclosed herein. For example, FIG. 27 is a schematic diagram of an example configuration of a server computing device 2700, in accordance with some embodiments of the present disclosure. Server computing devices having an architecture similar to server computing device 2700 may be used to implement one or more of the computing systems shown in FIG. 1, such as genotyping computing device 110. In the example embodiment, server computing device 2700 includes processor 2705 for executing instructions (not shown) stored in a memory 2710. In an embodiment, processor 2705 may include one or more processing units (e.g., in a multi-core configuration). The instructions may be executed within various different operating systems, such as UNIX®, LINUX® (LINUX is a registered trademark of Linus Torvalds), Microsoft Windows®, etc. It should also be appreciated that upon initiation of a computer-based method, various instructions may be executed during initialization. Some operations may be required in order to perform one or more processes described herein, while other operations may be more general or specific to a particular programming language (e.g., C, C #, C++, Java, or other suitable programming languages, etc.).

In the example embodiment, processor 2705 is operatively coupled to a communication interface 2715 such that server computing device 2700 is capable of communicating with a remote device, such as a user or system administrator computing system (not shown) or another server computing device 2700.

In the example embodiment, processor 2705 is also operatively coupled to a storage device 2730, which may be, for example, a computer-operated hardware unit suitable for storing or retrieving data. In some embodiments, storage device 2730 is integrated into server computing device 2700. For example, device 2700 may include one or more hard disk drives as storage device 2730. In other embodiments, storage device 2730 is external to device 2700 and may be accessed by a plurality of server computing devices 2700. For example, storage device 2730 may include multiple storage units such as hard disks or solid-state disks in a redundant array of inexpensive disks (RAID) configuration. Storage device 2730 may include a storage area network (SAN) or a network attached storage (NAS) system. Storage device 2730 may be used as a repository for one or more databases or other data structures for storing various data elements received, processed, and/or generated by genotyping computing device 110. For example, storage device 2730 is used to implement database 120 (shown in (FIGS. 1 and 2).

In some embodiments, processor 2705 is operatively coupled to storage device 2730 via an optional storage interface 2720. Storage interface 2720 may include, for example, a component capable of providing processor 2705 with access to storage device 2730. In one embodiment, storage interface 2720 further includes one or more of an Advanced Technology Attachment (ATA) adapter, a Serial ATA (SATA) adapter, a Small Computer System Interface (SCSI) adapter, a RAID controller, a SAN adapter, a network adapter, or a similarly capable component providing processor 2705 with access to storage device 2730.

Memory area 2710 may include, but is not limited to, random-access memory (RAM) such as dynamic RAM (DRAM) or static RAM (SRAM), read-only memory (ROM), erasable programmable read-only memory (EPROM), electrically erasable programmable read-only memory (EEPROM), non-volatile RAM (NVRAM), and magneto-resistive random-access memory (MRAM). The above memory types are for example only, and are thus not limiting as to the types of memory usable for storage of a computer program.

Figure 28:
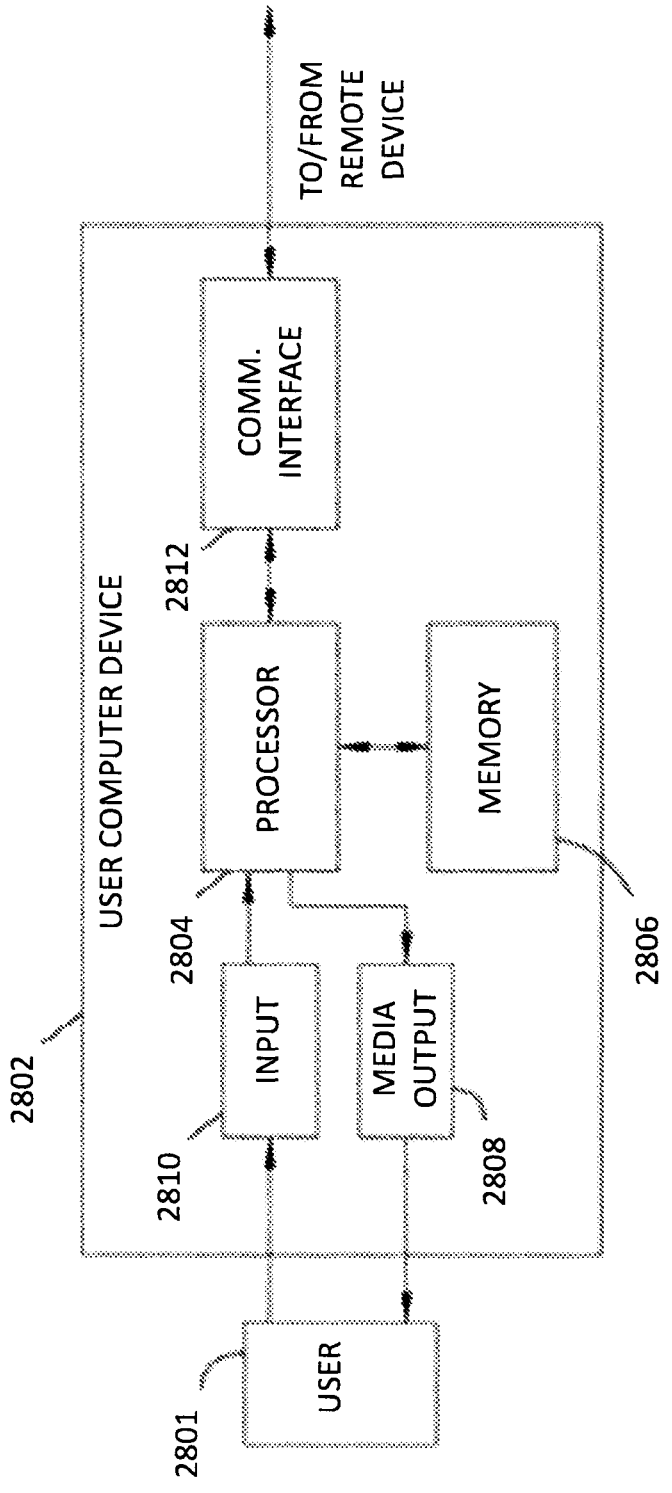
FIG. 28 is a block diagram of a user computing device that may be used with the computer system of FIG. 1, in accordance with an embodiment of the present disclosure.

Example user computing devices are disclosed herein. For example, FIG. 28 illustrates an example configuration of a user computing device 2802. User computing device 2802 includes a processor 2804 for executing instructions. In some embodiments, executable instructions are stored in a memory area 2806. Processor 2804 may include one or more processing units (e.g., in a multi-core configuration). Memory area 2806 is any device allowing information such as executable instructions and/or other data to be stored and retrieved. Memory area 2806 may include one or more computer-readable media.

User computing device 2802 also includes at least one media output component 2808 for presenting information to a user. Media output component 2808 is any component capable of conveying information to user. In some embodiments, media output component 2808 includes an output adapter such as a video adapter and/or an audio adapter. An output adapter is operatively coupled to processor 2804 and operatively couplable to an output device such as a display device (e.g., a liquid crystal display (LCD), organic light emitting diode (OLED) display, cathode ray tube (CRT), or "electronic ink" display) or an audio output device (e.g., a speaker or headphones). For example, a user may view genotyping information via media output component 2808.

In some embodiments, user computing device 2802 includes an input device 2810 for receiving input from user. Input device 2810 may include, for example, a keyboard, a pointing device, a mouse, a stylus, a touch sensitive panel (e.g., a touch pad or a touch screen), a camera, a gyroscope, an accelerometer, a position detector, and/or an audio input device. A single component such as a touch screen may function as both an output device of media output component 2808 and input device 2810.

User computing device 2802 may also include a communication interface 2812, which is communicatively couplable to a remote device such as a server system or a web server operated by a bioregistry. Communication interface 2812 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Machine learning methods are disclosed herein. The computer-implemented methods discussed herein may include additional, less, or alternate actions, including those discussed elsewhere herein. The methods may be implemented via one or more local or remote processors, transceivers, servers and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally, or alternatively, the machine learning programs may be trained by inputting sample data sets or certain data into the programs, such as sequencing data (e.g., long-read sequencing data) 220, first datasets 222 (e.g., datasets excluding reads with sequence artifacts), second datasets 224 (e.g., datasets excluding sequences with structural artifacts), third datasets 226 (e.g., datasets including sequencing reads categorized by allele), fourth datasets 228 (e.g., datasets including consensus reads for each allele), fifth datasets 230 (e.g., datasets including the corresponding amino-acid sequence for each allele), and/or any other information used, received, and/or generated by genotyping computing device 110. The machine learning programs may utilize deep learning algorithms that may be primarily focused on pattern recognition, and may be trained after processing multiple examples. The machine learning programs may include Bayesian Program Learning (BPL), voice recognition and synthesis, image or object recognition, optical character recognition, and/or natural language processing-either individually or in combination. The machine learning programs may also include natural language processing, semantic analysis, automatic reasoning, and/or machine learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. In some embodiments, machine learning techniques may be used to extract data about a particular allele based on sequencing reads (e.g., sequencing reads without sequence artifacts and/or structural artifacts).

In some embodiments, the voice bots or chatbots discussed herein may be configured to utilize ML and/or AI techniques. For instance, the voice bot or chatbot may be an AI chatbot. The voice bot or chatbot may employ supervised or unsupervised machine learning techniques, which may be followed by, and/or used in conjunction with, reinforced or reinforcement learning techniques.

As will be appreciated based upon the foregoing specification, the above-described embodiments of the disclosure may be implemented using computer programming or engineering techniques including computer software, firmware, hardware or any combination or subset thereof. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), SD card, memory device and/or any transmitting/receiving medium, such as the Internet or other communication network or link. The article of manufacture containing the computer code may be made and/or used by executing the code directly from one medium, by copying the code from one medium to another medium, or by transmitting the code over a network.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In some embodiments, a computer program is provided, and the program is embodied on a computer readable medium. In an example embodiment, the system is executed on a single computer system, without requiring a connection to a server computer. In a further embodiment, the system is being run in a Windows® environment (Windows is a registered trademark of Microsoft Corporation, Redmond, Washington). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality.

In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes. The present embodiments may enhance the functionality and functioning of computers and/or computer systems.

As used herein, an element or step recited in the singular and preceded by the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

The patent claims at the end of this document are not intended to be construed under 35 U.S.C. § 112(f) unless traditional means-plus-function language is expressly recited, such as "means for" or "step for" language being expressly recited in the claim(s).

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system for determining genotype of a gene comprising at least one repeat region, the system comprising:
   at least one memory storing computer-executable instructions; and
   at least one processor in communication with the at least one memory, wherein the at least one processor is configured to execute the computer-executable instructions to:
      generate a training dataset comprising sequences containing no structural artifacts and one or more previously determined allele classifications, wherein a structural artifact comprises a sequence with unknown copy numbers compared with exon or subunit structure in a reference gene;
      train a machine-learning model using the training dataset;
      receive an input set of genetic long-read sequencing data;
      measure at least one repeat structure of at least one sequence read of the genetic long-read sequencing data and remove sequence reads with abnormal repeat structures to generate a first dataset, the first dataset excluding sequence reads with sequence artifacts;
      remove sequence reads of the first dataset which contain structural artifacts to generate a second dataset, the second dataset excluding sequences with structural artifacts;
      apply input data to the trained machine-learning model to generate a third dataset, the input data comprising sequence reads of the second dataset, and the third dataset including sequencing reads categorized by allele;
      generate a consensus sequence for each allele in the third dataset to generate a fourth dataset of consensus reads for all alleles in the third dataset;
      translate each allele of the fourth dataset to generate a fifth dataset, the fifth dataset including a corresponding amino-acid sequence of each allele;
      determine a protein-altering variant status based on the amino-acid sequences of the fifth dataset;
      analyze a plurality of alleles categorized by the trained machine-learning model to determine one or more adjustments to weight values; and
      retrain the trained machine-learning model with the one or more adjustments to weight values such that the one or more adjustments to weight values modify subsequent categorization of alleles.

2. The system of claim 1, wherein the at least one processor is further configured to execute the computer-executable instructions to compare amino-acid sequence lengths of the fifth dataset to an expected length of an amino-acid reference sequence, to generate a sixth dataset of protein-truncating variants.

3. The system of claim 2, wherein the at least one processor is further configured to execute the computer-executable instructions to classify the protein-truncating variants of the sixth dataset as stop-gain variants or frame-shift variants.

4. The system of claim 2, wherein the expected length of an amino-acid reference sequence is a size range as determined by a range of lengths of variants of the gene known to exist.

5. The system of claim 1, wherein the training includes using a backpropagation algorithm to reduce a difference between one or more outputs of the model and the one or more previously determined allele classifications, and wherein the at least one processor is further configured to execute the computer-executable instructions to exclude sequencing artifacts by detecting read structure by alignment, grouping sequencing reads by structure, sorting read groups by frequency, and identifying novel alleles with previously unknown copy numbers.

6. The system of claim 1, wherein the at least one processor is further configured to execute the computer-executable instructions to exclude structural artifacts by mapping sequences from known references of each individual repeat to the sequencing reads to determine the structure of the reads, and exclude reads that include repeat structures that are not representative of known variants of the gene, and are thus deemed to be sequencing artifacts.

7. The system of claim 1, wherein at least one output of the model comprises classification of sequence reads of the second dataset as either copy number heterogeneous or copy number homogeneous.

8. The system of claim 7, wherein the at least one processor is further configured to execute the computer-executable instructions to, classify sequence reads of the second dataset as copy number heterogeneous or copy number homogeneous by:

grouping the sequencing reads of the second dataset by structure;

ordering the groups by frequency;

identifying a first frequent group and, if existing, a second frequent group of reads; and categorizing the gene as copy number homogeneous or copy number heterozygous based on differences in length of the first and second frequent groups, and frequency of each group in the second dataset.

9. The system of claim 8, wherein the at least one processor is further configured to execute the computer-executable instructions to, during execution of the model, for sequence reads classified as copy number homogeneous, separate the sequence reads for each allele by analyzing heterozygous SNPs and indels in their DNA sequence.

10. The system of claim 9, wherein the at least one processor is further configured to execute the computer-executable instructions to separate reads for each allele by analyzing heterozygous SNPs and indels in their DNA sequence using a k-means clustering algorithm.

11. A computer-implemented method for determining a genotype of a repeat rich gene, the method implemented using a system including a computing device including a processor communicatively coupled to memory device, the method comprising:

generating a training dataset comprising sequences containing no structural artifacts and one or more previously determined allele classifications, wherein a structural artifact comprises a sequence with unknown copy numbers compared with exon or subunit structure in a reference gene;

training a machine-learning model using the training dataset;

receiving an input set of genetic long-read sequencing data;

measuring at least one repeat structure of at least one sequence read of the genetic long-read sequencing data and remove sequence reads with abnormal repeat structures to generate a first dataset, the first dataset excluding sequence reads with sequence artifacts;

removing sequence reads of the first dataset which contain structural artifacts to generate a second dataset, the second dataset excluding sequences with structural artifacts;

applying input data to the trained machine-learning model to generate a third dataset, the input data comprising sequence reads of the second dataset, and the third dataset including sequencing reads categorized by allele;

generating a consensus sequence for each allele in the third dataset to generate a fourth dataset of consensus reads for all alleles in the third dataset;

translating each allele of the fourth dataset to generate a fifth dataset, the fifth dataset including a corresponding amino-acid sequence of each allele; and determining a protein-altering variant status based on the amino-acid sequences of the fifth dataset.

12. The computer-implemented method of claim 11, further comprising comparing amino-acid sequence lengths of the fifth dataset to an expected length of an amino-acid reference sequence, to generate a sixth dataset of protein-truncating variants.

13. The computer-implemented method of claim 12, further comprising classifying the protein-truncating variants of the sixth dataset as stop-gain variants or frameshift variants.

14. The computer-implemented method of claim 12, wherein the expected length of an amino-acid reference sequence is a size range as determined by a range of lengths of variants of the gene known to exist.

15. The computer-implemented method of claim 11, further comprising wherein the training includes using a backpropagation algorithm to reduce a difference between one or more outputs of the model and the one or more previously determined allele classifications, and excluding sequencing artifacts by detecting read structure by alignment, grouping sequencing reads by structure, sorting read groups by frequency, and identifying novel alleles with previously unknown copy numbers.

16. The computer-implemented method of claim 11, exclude structural artifacts by mapping sequences from known references of each individual repeat to the sequencing reads to determine the structure of the reads, and excluding reads that include repeat structures that are not representative of known variants of the gene, and are thus deemed to be sequencing artifacts.

17. The computer-implemented method of claim 11, wherein at least one output of the model comprises classification of sequence reads of the second dataset as either copy number heterogeneous or copy number homogeneous.

18. The computer-implemented method of claim 17, wherein classifying sequence reads as copy number heterogeneous or copy number homogeneous comprises:

grouping the sequencing reads of the second dataset by structure;

ordering the groups by frequency;

identifying a first frequent group and, if existing, a second frequent group of reads; and categorizing the gene as copy number homogeneous or copy number heterozygous based on differences in length of the first and second frequent groups, and frequency of each group in the second dataset.

19. The computer-implemented method of claim 18, further comprising, during execution of the model, separating reads for each allele by analyzing heterozygous SNPs and indels in their DNA sequence using a k-means clustering algorithm.

20. At least one non-transitory computer-readable storage medium having computer-executable instructions embodied thereon, wherein when executed by at least one processor, the computer-executable instructions cause the at least one processor to:

generate a training dataset comprising sequences containing no structural artifacts and one or more previously determined allele classifications, wherein a structural artifact comprises a sequence with unknown copy numbers compared with exon or subunit structure in a reference gene;

train a machine-learning model using the training dataset;

receive an input set of genetic long-read sequencing data;

measure at least one repeat structure of at least one sequence read of the genetic long-read sequencing data and remove sequence reads with abnormal repeat structures to generate a first dataset, the first dataset excluding sequence reads with sequence artifacts;

remove sequence reads of the first dataset to generate a second dataset, the second dataset excluding sequences with structural artifacts;

apply input data to the trained machine-learning model to generate a third dataset, the input data comprising sequence reads of the second dataset, and the third dataset including sequencing reads categorized by allele;

generate a consensus sequence for each allele in the third dataset to generate a fourth dataset of consensus reads for all alleles in the third dataset;

translate each allele of the fourth dataset to generate a fifth dataset, the fifth dataset including a corresponding amino-acid sequence of each allele;

determine a protein-altering variant status based on the amino-acid sequences of the fifth dataset; and retrain the trained machine-learning model with one or more adjustments to weight values such that the one or more adjustments to weight values modify subsequent categorization of alleles.

* * * * *